(12) United States Patent
Calas et al.

(10) Patent No.: US 6,620,910 B1
(45) Date of Patent: Sep. 16, 2003

(54) PEPTIDE COMPOUNDS ANALOGUES OF THE GLUCAGON-LIKE PEPTIDE-1 (7-37)

(75) Inventors: Bernard Calas, Montpellier (FR); Gérard Grassy, Perols (FR); Alain Chavanieu, Assas (FR); Cyril Sarrauste de Menthiere, Montpellier (FR); Pierre Renard, Le Chesnay (FR); Bruno Pfeiffer, Saint Leu la Foret (FR); Dominique Manechez, Villeneuve D'Ascq (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/268,578

(22) Filed: Mar. 15, 1999

(30) Foreign Application Priority Data

Apr. 10, 1998 (FR) .............................. 98 04559

(51) Int. Cl.$^7$ .............................. A61K 38/16
(52) U.S. Cl. .......................... 530/324; 530/308; 514/12
(58) Field of Search ................ 514/12, 3, 21; 530/300, 324, 303, 308; 424/185.1

(56) References Cited

PUBLICATIONS

Exp. Clin. Endocrinol. Diabetes 105, 187–195 (1997).
BioEssays 20, 642–651 (1998).
Eur. J. Pharmacol. 440, 269–279 (2002).

*Primary Examiner*—Christopher S. F. Low
*Assistant Examiner*—David Lukton
(74) *Attorney, Agent, or Firm*—The Firm of Hueschen and Sage

(57) ABSTRACT

Compound of formula (I):

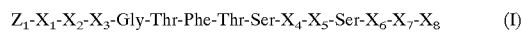

$$Z_1\text{-}X_1\text{-}X_2\text{-}X_3\text{-Gly-Thr-Phe-Thr-Ser-}X_4\text{-}X_5\text{-Ser-}X_6\text{-}X_7\text{-}X_8 \qquad (I)$$

wherein:

$Z_1$, substituent of the terminal amino group, represents hydrogen, alkyl or acyl, or arylcarbonyl, heteroarylcarbonyl, arylalkylcarbonyl, heteroarylcarbonyl, aryloxycarbonyl, arylalkoxycarbonyl or alkoxycarbonyl each of which is optionally substituted, $Z_2$ (SEQ ID NO: 1), substituent of the terminal carbonyl group, represents hydroxy, alkoxy or optionally substituted amino, $X_1$ to $X_{14}$ each represents an amino acid residue having the D or L configuration as defined in the description, $X_{15}$ represents a bond or an arginine residue (Arg).

Medicinal products containing the same are useful as 'GLP-1 agonists.

25 Claims, No Drawings

SEQUENCE LISTING

<160> NUMBER OF SEQ ID NOS: 59

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: MOD_RES
<222> LOCATION: (1)
<223> OTHER INFORMATION: an amino acid which may be a natural or
      non-natural amino acid residue having the D or L configuration;
      a natural or non-natural cyclic amino acid residue having the D or
      L configuration; or a 3-amino-3-(2-furyl)propanoic acid residue
<221> NAME/KEY: MOD_RES
<222> LOCATION: (2)
<223> OTHER INFORMATION: an amino acid which may be a natural or
      non-natural amino acid residue having the D or L configuration;
      a natural or non-natural cyclic amino acid residue having the D -continued

```
       or L configuration; or a 3-amino-3-(2- furyl)propanoic acid
       residue
<221> NAME/KEY: MOD_RES
<222> LOCATION: (3)
<223> OTHER INFORMATION: an amino acid which may be a natural or
       non-natural amino acid residue having the D or L configuration; a
       natural or non-natural cyclic amino acid residue having the D or
       L configuration; or a 3-amino-3-(2-furyl)propanoic acid residue
<221> NAME/KEY: MOD_RES
<222> LOCATION: (9)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (10)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (12)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (13)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (14)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (19)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (21)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (22)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (23)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (25)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (26)
<223> OTHER INFORMATION: an amino acid which may be a natural or
       non-natural amino acid residue having the D or L configuration; a
       natural or non-natural cyclic amino acid residue having the D or L
       configuration; or a 3-amino-3-(2-furyl)propanoic acid residue
<221> NAME/KEY: MOD_RES
<222> LOCATION: (30)
<223> OTHER INFORMATION: may be an Arg residue or missing

<400> SEQUENCE: 1
```

```
Xaa Xaa Xaa Gly Thr Phe Thr Ser Xaa Xaa Ser Xaa Xaa Xaa Glu Gly
 1               5                  10                  15

Gln Ala Xaa Lys Xaa Xaa Xaa Ala Xaa Xaa Val Lys Gly Xaa Gly
            20                  25                  30
```

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: MOD_RES
<222> LOCATION: (1)
<223> OTHER INFORMATION: the D or L configuration of a natural or
      non-natural amino acid residue having an aromatic character side
      chain
<221> NAME/KEY: MOD_RES
<222> LOCATION: (2)
<223> OTHER INFORMATION: the D or L configuration of a natural or
      non-natural amino acid residue having an aliphatic character side
      chain
<221> NAME/KEY: MOD_RES
<222> LOCATION: (3)
<223> OTHER INFORMATION: the D or L configuration of a natural or
      non-natural amino acid residue having a side chain capable of
      establishing ionic interactions
<221> NAME/KEY: MOD_RES
<222> LOCATION: (30)
<223> OTHER INFORMATION: may be Arg or missing

<400> SEQUENCE: 2

```
Xaa Xaa Xaa Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Xaa Gly
            20                  25                  30
```

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (14)
<223> OTHER INFORMATION: D-configuration of Leu

<400> SEQUENCE: 3

```
His Ala Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Gly Arg Gly
            20                  25                  30
```

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (26)
<223> OTHER INFORMATION: D-configuration of Leu

<400> SEQUENCE: 4

```
Trp Ala Glu Gly Thr Phe Thr Ser Asp Val Ser Ser Tyr Leu Glu Gly
 1               5                  10                  15
```

```
Gln Ala Ala Lys Glu Phe Ile Ala Trp Xaa Val Lys Gly Arg Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 5

Trp Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 6

His Ala Gln Gly Thr Phe Thr Ser Asp Val Ser Ser Val Leu Glu Gly
  1               5                  10                  15

Gln Ala Ala Lys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 7

His Ala His Gly Thr Phe Thr Ser Asp Val Ser Ser Val Leu Glu Gly
  1               5                  10                  15

Gln Ala Ala Lys Glu Phe Ile Ala Trp Leu Val Lys Gly Arg Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (3)
<223> OTHER INFORMATION: D-configuration of Glu

<400> SEQUENCE: 8

His Ala Xaa Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
            20                  25                  30

<210> SEQ ID NO 9
<211> LENGTH: 30
<212> TYPE: PRT
<213> ORGANISM: Artificial Sequence
```

```
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala

<400> SEQUENCE: 9

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 10

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 11

His Leu Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 12

His Val Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: MOD_RES
<222> LOCATION: (1)
<223> OTHER INFORMATION: 3-amino-3-(2-furyl)propanoic acid (Afp)

<400> SEQUENCE: 13
```

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 14

His Ala Asp Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 15

His Ala Ser Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 16

His Ala Lys Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala

<400> SEQUENCE: 17

Phe Xaa Glu Gly Thr Phe Thr Ser Asp Val Ser Lys Tyr Leu Glu Gly
 1               5                  10                  15

Gln Ala Val Lys Glu Phe Ile Ala Trp Leu Val Lys Gly Gly
            20                  25                  30

```
<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration Ala
<221> NAME/KEY: VARIANT
<222> LOCATION: (14)
<223> OTHER INFORMATION: D-configuration of Leu

<400> SEQUENCE: 18

Phe Xaa Gln Gly Thr Phe Thr Ser Asp Val Ser Ser Val Xaa Glu Gly
 1               5                  10                  15

Gln Ala Ala Lys Glu Phe Ile Ala Trp Leu Val Lys Gly Gly
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 19

His Ala Leu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 20

His Ala Met Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 21

His Ala Glu Gly Thr Phe Thr Ser Asp Val Ser Ser Tyr Leu Glu Gly
 1               5                  10                  15

Gln Ala Ala Lys Glu Trp Ile Ala Trp Leu Val Lys Gly Gly
            20                  25                  30

<210> SEQ ID NO 22
<211> LENGTH: 30
<212> TYPE: PRT
<213> ORGANISM: Artificial Sequence
<220> FEATURE:
```

<223> OTHER INFORMATION: Description of Artificial Sequence:
    glucagon-like peptides

<400> SEQUENCE: 22

His Ala Glu Gly Thr Phe Thr Ser Asp Val Ser Ser Tyr Leu Glu Gly
  1               5                  10                  15

Gln Ala Ala Lys Glu Ile Ile Ala Trp Leu Val Lys Gly Gly
             20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence:
    glucagon-like peptides

<400> SEQUENCE: 23

His Ala Glu Gly Thr Phe Thr Ser Asp Val Ser Ser Tyr Leu Glu Gly
  1               5                  10                  15

Gln Ala Ala Lys Glu Val Ile Ala Trp Leu Val Lys Gly Gly
             20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence:
    glucagon-like peptides

<400> SEQUENCE: 24

His Ala Glu Gly Thr Phe Thr Ser Asp Val Ser Ser Tyr Leu Glu Gly
  1               5                  10                  15

Gln Ala Ala Lys Glu His Ile Ala Trp Leu Val Lys Gly Gly
             20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence:
    glucagon-like peptides

<400> SEQUENCE: 25

His Ala Glu Gly Thr Phe Thr Ser Asp Val Ser Ser Tyr Leu Glu Gly
  1               5                  10                  15

Gln Ala Ala Lys Glu Asp Ile Ala Trp Leu Val Lys Gly Gly
             20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence:
    glucagon-like peptides

<400> SEQUENCE: 26

His Ala Glu Gly Thr Phe Thr Ser Asp Val Ser Ser Tyr Leu Glu Gly
  1               5                  10                  15

Gln Ala Ala Lys Glu Phe Leu Ala Trp Leu Val Lys Gly Gly
             20                  25                  30

```
<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 27

His Ala Glu Gly Thr Phe Thr Ser Asp Val Ser Ser Tyr Leu Glu Gly
 1               5                  10                  15

Gln Ala Ala Lys Glu Phe Val Ala Trp Leu Val Lys Gly Gly
             20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 28

His Ala Glu Gly Thr Phe Thr Ser Asp Val Ser Ser Tyr Leu Glu Gly
 1               5                  10                  15

Gln Ala Ala Lys Glu Phe Tyr Ala Trp Leu Val Lys Gly Gly
             20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 29

His Ala Glu Gly Thr Phe Thr Ser Asp Val Ser Ser Tyr Leu Glu Gly
 1               5                  10                  15

Gln Ala Ala Lys Glu Phe Arg Ala Trp Leu Val Lys Gly Gly
             20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 30

His Ala Glu Gly Thr Phe Thr Ser Asp Val Ser Ser Tyr Leu Glu Gly
 1               5                  10                  15

Gln Ala Ala Lys Glu Phe Glu Ala Trp Leu Val Lys Gly Gly
             20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 31
```

-continued

```
Phe Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30
```

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 32

```
His Ala Lys Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 33

```
His Ala Met Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 34

```
His Ala Leu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 35

```
His Ala Ser Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 36
<211> LENGTH: 31
<212> TYPE: PRT
<213> ORGANISM: Artificial Sequence

```
<220> FEATURE:
<223> OTHER INFORMATION: Description of Artificial Sequence:
      glucagon-like peptides
<221> NAME/KEY: VARIANT
<222> LOCATION: (26)
<223> OTHER INFORMATION: D-configuration of Leu

<400> SEQUENCE: 36

His Ala Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Gly Arg Gly
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (9)
<223> OTHER INFORMATION: Aib

<400> SEQUENCE: 37

His Xaa Glu Gly Thr Phe Thr Ser Xaa Val Ser Ser Tyr Leu Glu Gly
 1               5                  10                  15

Gln Ala Ala Lys Glu Phe Ile Ala Trp Leu Val Lys Gly Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (21)
<223> OTHER INFORMATION: Nva

<400> SEQUENCE: 38

His Xaa Glu Gly Thr Phe Thr Ser Asp Val Ser Ser Tyr Leu Glu Gly
 1               5                  10                  15

Gln Ala Ala Lys Xaa Phe Ile Ala Trp Leu Val Lys Gly Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (21)
<223> OTHER INFORMATION: Nle

<400> SEQUENCE: 39

His Xaa Glu Gly Thr Phe Thr Ser Asp Val Ser Ser Tyr Leu Glu Gly
 1               5                  10                  15
```

```
                  1               5                  10                 15
Gln Ala Ala Lys Xaa Phe Ile Ala Trp Leu Val Lys Gly Gly
                 20                 25                 30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (21)
<223> OTHER INFORMATION: Aib

<400> SEQUENCE: 40

His Xaa Glu Gly Thr Phe Thr Ser Asp Val Ser Ser Tyr Leu Glu Gly
 1               5                  10                 15
Gln Ala Ala Lys Xaa Phe Ile Ala Trp Leu Val Lys Gly Gly
                 20                 25                 30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (22)
<223> OTHER INFORMATION: naphthylalanine (Nal)

<400> SEQUENCE: 41

His Xaa Glu Gly Thr Phe Thr Ser Asp Val Ser Ser Tyr Leu Glu Gly
 1               5                  10                 15
Gln Ala Ala Lys Glu Xaa Ile Ala Trp Leu Val Lys Gly Gly
                 20                 25                 30

<210> SEQ ID NO 42
<211> LENGTH: 31
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (22)..(23)
<223> OTHER INFORMATION: naphthyalanine (Nal)

<400> SEQUENCE: 42

His Xaa Glu Gly Thr Phe Thr Ser Asp Val Ser Ser Tyr Leu Glu Gly
 1               5                  10                 15
Gln Ala Ala Lys Glu Xaa Xaa Ile Ala Trp Leu Val Lys Gly Gly
                 20                 25                 30

<210> SEQ ID NO 43
<211> LENGTH: 30
<212> TYPE: PRT
<213> ORGANISM: Artificial Sequence
```

```
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (22)
<223> OTHER INFORMATION: phenylglycine (Phg)

<400> SEQUENCE: 43

His Xaa Glu Gly Thr Phe Thr peptides

<221> NAME/KEY: VARIANT
<222> LOCATION: (2)
<223> OTHER INFORMATION: D-configuration of Ala
<221> NAME/KEY: MOD_RES
<222> LOCATION: (23)
<223> OTHER INFORMATION: Nva

<400> SEQUENCE: 44

His Xaa Glu Gly Thr Phe Thr Ser Asp Val Ser Ser Tyr Leu Glu Gly
 1               5                  10                  15

Gln Ala Ala Lys Glu Phe Xaa Ala Trp Leu Val Lys Gly Gly
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (23)
<223> OTHER INFORMATION: Nle

<400> SEQUENCE: 45

His Xaa Glu Gly Thr Phe Thr Ser Asp Val Ser Ser Tyr Leu Glu Gly
 1               5                  10                  15

Gln Ala Ala Lys Glu Phe Xaa Ala Trp Leu Val Lys Gly Gly
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala
<221> NAME/KEY: MOD_RES
<222> LOCATION: (9)
<223> OTHER INFORMATION: Aib
<221> NAME/KEY: MOD_RES
<222> LOCATION: (21)
<223> OTHER INFORMATION: Aib
<221> NAME/KEY: MOD_RES
<222> LOCATION: (22)
<223> OTHER INFORMATION: naphthylalanine (Nal)
<221> NAME/KEY: MOD_RES
<222> LOCATION: (23)
<223> OTHER INFORMATION: Nle

<400> SEQUENCE: 46

His Xaa Glu Gly Thr Phe Thr Ser Xaa Val Ser Ser Tyr Leu Glu Gly
```

```
                1               5                  10                 15
Gln Ala Ala Lys Xaa Xaa Xaa Ala Trp Leu Val Lys Gly Gly
                20                 25                 30

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala

<400> SEQUENCE: 47

His Xaa Glu Gly Thr Phe Thr Ser Asp Val Ser Ser Tyr Leu Glu Gly
 1               5                  10                 15
Gln Ala Ala Lys Glu Phe Ile Ala Trp Leu Val Lys Gly Gly
                20                 25                 30

<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 48

His Ala Glu Gly Thr Phe Thr Ser Asp Val Ser Ser Tyr Leu Glu Gly
 1               5                  10                 15
Gln Ala Ala Lys Glu Phe Ile Ala Trp Leu Val Lys Gly Gly
                20                 25                 30

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 49

His Ala Asp Gly Thr Phe Thr Ser Asp Val Ser Ser Tyr Leu Glu Gly
 1               5                  10                 15
Gln Ala Ala Lys Glu Phe Ile Ala Trp Leu Val Lys Gly Gly
                20                 25                 30

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala

<400> SEQUENCE: 50

Phe Xaa Glu Gly Thr Phe Thr Ser Asp Val Ser Lys Tyr Leu Glu Gly
 1               5                  10                 15
Gln Ala Val Lys Glu Phe Ile Ala Trp Leu Val Lys Gly Gly
                20                 25                 30
```

```
<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 51

His Ala Met Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 52

His Ala Glu Gly Thr Phe Thr Ser Asp Val Ser Ser Tyr Leu Glu Gly
  1               5                  10                  15

Gln Ala Ala Lys Glu Trp Ile Ala Trp Leu Val Lys Gly Gly
             20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala

<400> SEQUENCE: 53

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 54

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Gly
             20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
```

<400> SEQUENCE: 55

His Ala Asp Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-configuration of Ala

<400> SEQUENCE: 56

Phe Xaa Glu Gly Thr Phe Thr Ser Asp Val Ser Lys Tyr Leu Glu Gly
1               5                   10                  15

Gln Ala Val Lys Glu Phe Ile Ala Trp Leu Val Lys Gly Gly
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides

<400> SEQUENCE: 57

His Ala Met Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides
<221> NAME/KEY: VARIANT
<222> LOCATION: (2)
<223> OTHER INFORMATION: D-Configuration of Ala

<400> SEQUENCE: 58

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence:
      glucagon-like peptides -continued

<400> SEQUENCE: 59

```
His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly
             20                  25                  30
```

PEPTIDE COMPOUNDS ANALOGUES OF THE GLUCAGON-LIKE PEPTIDE-1 (7-37)

TITLE OF THE INVENTION

The present invention relates to new peptide compounds that are analogues of Glucagon-Like Peptide-1 (7-37).

BACKGROUND OF THE INVENTION

The Glucagon-Like Peptides-1 (7-37) and (7-36) $NH_2$ ('GLP-1) are peptides of intestinal origin that are heavily involved in the control of glucidic homeostasis. These peptides are the principal mediators of the "entero-insular axis" and act by bindings to specific receptors.

'GLP-1 is predominantly active in the pancreas where it exerts a powerful stimulating effect on the secretion of insulin by β cells in a glucose-dependent manner (S. Mojsov et al., J. Clin. Invest., 1987, 79, 619; and J. J. Hoist, F.E.B.S. Letters, 1987, 211, 169). That stimulation is accompanied by stimulation of the release of somatostatin and inhibition of the release of glucagon.

In parallel with the above-mentioned effects on the pancreas, 'GLP-1 retards gastric emptying, reduces acid secretions and stimulates the peripheral utilisation of glucose in the muscles, liver and adipocytes. (M. L. Villanueva et al., Diabetologia, 1994, 37, 1163; D. J. Drucker, Diabetes, 1998, 47, 159).

Recent studies have also demonstrated that 'GLP-1 could have an effect on eating behaviour by inhibiting food and drink intake as a result of action on the satiety centres (M. D. Turton et al., Nature. 1996, 379, 69).

'GLP-1 thus has many potential therapeutic applications, especially in the treatment of non-insulin-dependent type II diabetes, obesity, and type I diabetes. Like many hormonal peptides, however, it has a rather short plasma half-life—less than 2 minutes (T. J. Kieffer et al., Endocrinology, 1995, 136, 3585)—which limits its use.

DESCRIPTION OF THE PRIOR ART

The use of the natural peptide $GLP_1$ (7-37) for its insulinotropic properties has been described extensively, whether as the natural peptide $GLP_1$ (7-37) or $GLP_1$ (7-36) $NH_2$ on its own, in the form of salts, esters or amides (U.S. Pat. No. 5,616,492, WO 8706941, WO 9011 296), associated with phospholipids (WO 9318785) or associated with other hypoglycaeinic substances (WO 9318786). Analogues modified at some positions of the natural sequence have also been studied (EP 733 644, EP 708 179, EP 658 568, WO 91 11457) with the aim of devising compounds as potent as $GLP_1$ (7-37) that are better absorbed.

The compounds of the present invention have a novel structure derived from that of 'GLP-1 by modifications to several residues and/or by suppression of arginine at position 36. In addition to the fact that they are new, these compounds have valuable pharmacological properties as a result of their agonist character in relation to 'GLP-1 receptors. The modifications have the additional advantage of substantially increasing the metabolic stability of the compounds of the invention, thus giving them a duration of action superior to that of the natural peptide. Those properties make the compounds especially valuable in the treatment of pathologies in which 'GLP-1 is involved, especially in the treatment of non-insulin-dependent type II diabetes, obesity, and type I diabetes.

DETAILED DESCRIPTION OF THE INVENTION

The present invention relates to peptide compounds of the general formula (I):

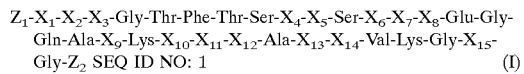
$Z_1$-$X_1$-$X_2$-$X_3$-Gly-Thr-Phe-Thr-Ser-$X_4$-$X_5$-Ser-$X_6$-$X_7$-$X_8$-Glu-Gly-Gln-Ala-$X_9$-Lys-$X_{10}$-$X_{11}$-$X_{12}$-Ala-$X_{13}$-$X_{14}$-Val-Lys-Gly-$X_{15}$-Gly-$Z_2$ SEQ ID NO: 1    (I)

wherein:

$Z_1$, substituent of the terminal amino group of the peptide of formula (I), represents a hydrogen atom, an alkyl group, a linear or branched ($C_1$–$C_6$)-acyl group, or an optionally substituted arylcarbonyl, optionally substituted heteroarylcarbonyl, optionally substituted arylalkylcarbonyl, optionally substituted heteroarylalkylcarbonyl, optionally substituted aryloxycarbonyl, optionally substituted arylalkoxycarbonyl or optionally substituted alkoxycarbonyl group, $Z_2$, substituent of the terminal carbonyl group of the peptide of formula (I), represents a hydroxy group, a linear or branched ($C_1$–$C_6$)-alkoxy group, or an amino group optionally substituted by one or two identical or different groups selected from linear or branched ($C_1$–$C_6$)-alkyl, optionally substituted aryl, optionally substituted heteroaryl, optionally substituted arylcarbonyl, optionally substituted heteroarylcarbonyl, optionally substituted arylalkylcarbonyl and optionally substituted heteroarylalkylcarbonyl, or by two groups that together with the nitrogen atom form a saturated ring having from 5 to 7 ring members), $X_1$ to $X_{14}$ each represents, independently of the others:
a natural or non-natural amino acid residue, having the D or L configuration, of the formula:

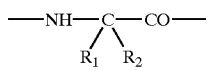
—NH—C—CO—
    / \
   $R_1$  $R_2$ wherein:
$R_1$ represents a hydrogen atom and $R_2$ represents a hydrogen atom or an alkyl, aminoalkyl (optionally substituted on the nitrogen atom by one or two alkyl, phenyl, benzyl, cycloalkyl, optionally substituted aryloxycarbonyl, optionally substituted arylalkoxycarbonyl and/or optionally substituted alkoxycarbonyl groups), thioalkyl (optionally substituted on the sulphur atom by an alkyl, phenyl, benzyl or cycloalknyl group), hydroxyalkyl (optionally substituted on the oxygen atom by an alkyl, phenyl, benzyl or cycloalkyl group), carboxyalkyl, carbamoylalkyl, guanidinoalkyl, cycloalkyl, cycloalkylalkyl, optionally substituted fused cycloalkyl, optionally substituted aryl, optionally substituted arylalkyl, optionally substituted heteroaryl or optionally substituted heteroarylalkyl group, or an imidazolyl or imidazolylalkyl group, or $R_1$ and $R_2$ together with the carbon atom carrying them, form a cycloalkyl or fused cycloalkyl group, or a natural or non-natural cyclic amino acid residue, having the D or L configuration, of the formula:

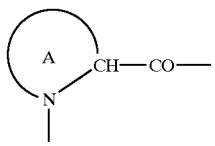

wherein A, together with the nitrogen and carbon atoms to which it is attached, forms a mono- or bi-cyclic group having from 5 to 11 ring members which is saturated, partially unsaturated or unsaturated, and is optionally substituted, or a 3-amino-3-(2-furyl)propanoic acid residue, and $X_{15}$ represents a bond or an arginine residue (Arg), and addition salts thereof with a pharmaceutically acceptable acid or base.

with the proviso that:

$X_{15}$ represents a bond:

when $X_1$ is a residue having the L or D configuration selected from tyrosine (Tyr), arginine (Arg), phenylalanine (Phe), ornithine (Orn), methionine (Met), proline (Pro), leucine (Leu), valine (Val), isoleucine (Ile), alanine (Ala), aspartic acid (Asp), glutamic acid (Glu), asparagine (Asn), glutamine (Gln) and histidine (His), and/or when $X_2$ represents a residue having the L or D configuration selected from serine (Ser), glycine (Gly), cysteine (Cys), sarcosine (Sar), alanine (Ala), proline (Pro), valine (Val), leucine (Leu), isoleucine (Ile) and threonine (Thr), and/or when $X_3$ represents an amino acid residue having the L or D configuration selected from glutamine (Gln), aspartic acid (Asp), threonine (Thr), asparagine (Asn) and glutamic acid (Glu), and/or when $X_5$ represents a tyrosine residue (Tyr), and/or when $X_6$ represents a lysine residue (Lys), and/or when $X_{10}$ represents an amino acid residue selected from glutamine (Gln), alanine (Ala), threonine (Thr), serine (Ser) and glycine (Gly), and/or when $X_{13}$ represents an amino acid residue selected from phenylalanine (Phe), valine (Val), leucine (Leu), isoleucine (Ile), alanine (Ala) and tyrosine (Tyr), it being understood that:

the residues $X_1$ to $X_{15}$ may not be so selected that the peptide obtained is identical to the natural peptide, the term "alkyl" denotes a linear or branched chain having from 1 to 6 carbon atoms, the term "cycloalkyl" denotes a saturated cyclic hydrocarbon group having from 3 to 8 ring members, the expression "fused cycloalkyl" denotes a bicyclic group having from 8 to 11 ring members composed of a saturated carbon-containing rings fused with a saturated or unsaturated ring optionally comprising one or two hetero atoms selected from nitrogen, oxygen and sulphur, for example an indan, tetrahydronaphthalene or tetrahydroquinoline group, the term "aryl" denotes a phenyl, naphthyl or biphenyl group, the term "heteroaryl" denotes a mono- or bi-cyclic group having from 5 to 11 ring members and containing from 1 to 4 hetero atoms selected from nitrogen, oxygen and sulphur, for example a furyl, pyridyl, thienyl or indolyl group, the term "arylcarbonyl" denotes an $R_a$—CO— group, the term "arylalkylcarbonyl" denotes and $R_a$—$R_b$—CO— group, the term "heteroarylcarbonyl" denotes an $R_c$—CO— group and the term "heteroarylalkylcarbonyl" denotes an $R_c$—$R_b$—CO— group, the term "aryloxycarbonyl" denotes an $R_a$—O—CO— group, the term "arylalkoxycarbonyl" denotes an $R_a$—$R_b$—O—CO— group and the term "alkoxycarbonyl" denotes an $R_b$—O—CO— group, in which groups $R_a$ represents an aryl group as defined hereinabove, $R_b$ represents an alkyl group as defined hereinabove and $R_c$ represents a heteroaryl group as defined hereinabove, the term "substituted" applied to the terms defined above denotes that the groups in question are substituted by one or more halogen atoms or linear or branched ($C_1$–$C_6$)-alkyl, hydroxy, linear or branched ($C_1$–$C_6$)-alkoxy, amino, cyano, nitro or linear or branched ($C_1$–$C_6$)-perhaloalkyl groups, each peptide bond —CO—NH— may optionally be replaced by a pseudopeptide bond selected from —$CH_2$—NH—, —NH—CO—, —CO—N($CH_3$)—, —$CH_2$—$CH_2$—, —$CH_2$—CO—, —$CH_2$—S—, —$CH_2$—SO—, —$CH_2$—$SO_2$—, —CH=CH— and —CO—$CH_2$—NH—.

Among the pharmaceutically acceptable acids there may be mentioned hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric acid etc.

Among the pharmaceutically acceptable bases there may be mentioned sodium hydroxide, potassium hydroxide, triethylamine, tert-butylamine etc. The present invention relates especially to peptide compounds of formula (I) wherein the residues $X_1$ to $X_{14}$ are selected as a function of the nature of their side chain, which may be of aromatic character or of aliphatic character, may be capable of establishin interactions of the hydrogen bonding type or capable of establishing ionic interactions, or may be of cyclic nature.

The natural or non-natural amino acid residues having the D or L configuration that have a side chain of aromatic character are represented by the following formula:

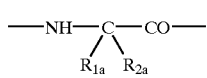

(a)

wherein:

$R_{1a}$ represents a hydrogen atom and $R_{2a}$ represents a cycloalkyl group fused with an unsaturated ring as defined hereinabove, and optionally substituted, or an optionally substituted aryl, optionally substituted arylalkyl, optionally substituted heteroaryl or optionally substituted heteroarylalkyl group, or an imidazolyl or imidazolylalkyl group, among which residues having a side chain of aromatic character there may be mentioned more specifically the phenylalanine (Phe), histidine (His), tyrosine (Tyr), tryptophan (Trp), homophenylalanine (Hof), halophenylalanine (for example 4-chlorophenylalanine (4-Cl-Phe)), dihalophenylalanine (for example 3,4-dichlorophenylalanine (3,4-di-Cl-Phe)), alkylphenylalanine (for example 4-methylphenylalanine (4-Me-Phe)), nitrophenylalanine (for example 4-nitrophenylalanine (4-NO$_2$-Phe)), 3-pyridylalanine (3-Pya), 2-thienylalanine (Tha), 2-furylalanine (Fua), 1-naphthylalanine (1-Nal), 2-naphthylalanine (2-Nal), phenylglycine (Phg) and 3-nitrotyrosine (3-NO$_2$-Tyr) residues, The natural or non-natural amino acid residues having the D or L configuration that have a side chain of aliphatic character are represented by the following formula:

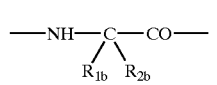

(b)

wherein:
R$_{1b}$ represents a hydrogen atom and R$_{2b}$ represents a hydrogen atom or an alkyl or cycloalkyl group, among which residues there may be mentioned more specifically the glycine (Gly), alanine (Ala), valine (Val), leucine (Leu), isoleucine (Ile), 2-aminobutyric acid (Abu), 2-aminoisobutyric acid (Aib), β-cyclohexylalanine (Cha), homoleucine (Hol), norleucine (Nle), norvaline (Nva) and tert-leucine (Tle) residues, The natural or non-natural amino acid residues having the D or L configuration that have a side chain capable of establishing interactions of the hydrogen bonding type are represented by the formula:

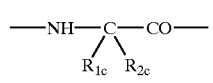

(c)

wherein:
R$_{1c}$ represents a hydrogen atom and R$_{2c}$ represents an aminoalkyl (optionally substituted on the nitrogen atom by an alkyl, phenyl, benzyl or cycloalkyl group), thioalkyl (optionally substituted on the sulphur atom by an alkyl, phenyl, benzyl or cycloalkyl group), hydroxyalkyl (optionally substituted on the oxygen atom by an alkyl, phenyl, benzyl or cycloalkyl group), carboxyalkyl, carbamoylalkyl or guanidinoalkyl group, among which residues there may be mentioned more specifically the methionine (Met), aspartic acid (Asp), glutamic acid (Glu), lysine (Lys), arginine (Arg), serine (Ser), threonine (Thr), cysteine (Cys), tyrosine (Tyr), asparagine (Asn), glutamine (Gln), tryptophan (Trp), diaminobutyric acid (Dab), diaminopropionic acid (Dapa), ornithine (Orn) and benzylcysteine (Bcy) residues, The natural or non-natural amino acid residues having the D or L configuration that have a side chain capable of establishing interactions of the ionic type are represented by the formula:

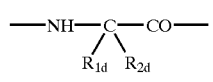

(d)

wherein:
R$_{1d}$ represents a hydrogen atom and R$_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, The non-natural amino acid residues having the D or L configuration that have a side chain of cyclic nature are represented by the following formula:

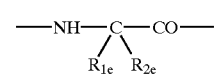

(e)

wherein:
R$_{1e}$ and R$_{2e}$ together form a cycloalkyl or a fused cycloalkyl group, among which residues there may be mentioned more specifically the 1-amino-1-cyclohexanecarboxylic acid (Acy), 2-aminoindan-2-carboxylic acid (Aic) and 2-aminotetraline-2-carboxylic acid (Atc) residues, X$_1$ preferably represents a natural or non-natural amino acid residue having the D or L configuration that has a side chain of aromatic character, represented by the formula (a), X$_2$ preferably represents a natural or non-natural amino acid residue having the D or L configuration that has a side chain of aliphatic character, represented by the formula (b), X$_3$ preferably represents a natural or non-natural amino acid residue having the D or L configuration that has a side chain capable of establishing ionic interactions, represented by the formula (d), X$_4$ preferably represents a natural or non-natural amino acid residue having the D or L configuration that has a side chain capable of establishing ionic interactions, represented by the formula (d), or a natural or non-natural amino acid residue having the D or L configuration that has a side chain of aliphatic character, represented by the formula (b), X$_5$ preferably represents a natural or non-natural amino acid residue having the D or L configuration that has a side chain of aliphatic character, represented by the formula (b), X$_6$ preferably represents a natural or non-natural amino acid residue having the D or L configuration that has a side chain capable of establishing ionic interactions, represented by the formula (d), X$_7$ preferably represents a natural or non-natural amino acid residue having the D or L configuration that has a side chain capable of establishing ionic interactions, represented by the formula (d), or a natural or non-natural amino acid residue having the D or L configuration that has a side chain of aliphatic character, represented by the formula (b), X$_8$ preferably represents a natural or non-natural amino acid residue having the D or L configuration that has a side chain of aliphatic character, represented by the formula (b), X$_9$ preferably represents a natural or non-natural amino acid residue having the D or L configuration that has a side chain of aliphatic character, represented by the formula (b), $X_{10}$ preferably represents a natural or non-natural amino acid residue having the D or L configuration that has a side chain capable of establishing ionic interactions, represented by the formula (d),
or a natural or non-natural amino acid residue having the D or L configuration that has a side chain of aliphatic character, represented by the formula (b), $X_{11}$ preferably represents a natural or non-natural amino acid residue having the D or L configuration that has a side chain of aromatic character, represented by the formula (a), $X_{12}$ preferably represents a natural or non-natural amino acid residue having the D or L configuration that has a side chain capable of establishing ionic interactions, represented by the formula (d),
or a natural or non-natural amino acid residue having the D or L configuration that has a side chain of aliphatic character, represented by the formula (b), $X_{13}$ preferably represents a natural or non-natural amino acid residue having the D or L configuration that has a side chain of aromatic character, represented by the formula (a), $X_{14}$ preferably represents a natural or non-natural amino acid residue having the D or L configuration that has a side chain of aliphatic character, represented by the formula (b), $X_{15}$ preferably represents a bond.

Preferably, in compounds of formula (I) $Z_1$ represents a hydrogen atom.

In compounds of formula (I), $Z_2$ preferably represents a group selected from hydroxy, linear or branched $(C_1–C_6)$-alkoxy, and amino. More specifically, $Z_2$ represents an amino group.

An advantageous aspect of the invention concerns compounds of formula (I) wherein:

$Z_1$ represents a hydrogen atom, $Z_2$ represents a group selected from hydroxy, linear or branched $(C_1–C_6)$-alkoxy, and amino, $X_1$ and $X_{11}$ represent a natural or non-natural amino acid residue having the D or L configuration and are independently selected from the amino acid residues having a side chain of aromatic character represented by the following formula:

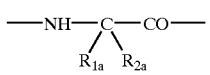
(a)

wherein:
$R_{1a}$ represents a hydrogen atom and $R_{2a}$ represents a cycloalkyl group fused with an unsaturated ring as defined hereinabove, and optionally substituted, or an optionally substituted aryl, optionally substituted arylalkyl, optionally substituted heteroaryl or optionally substituted heteroarylalkyl group, or an imidazolyl or imidazolylalkyl group, among which residues having a side chain of aromatic character there may be mentioned more specifically the phenylalanine (Phe), histidine (His), tyrosine (Tyr), tryptophan (Trp), homophenylalanine (Hof), halophenylalanine (for example 4-chlorophenylalanine (4-Cl-Phe)), dihalophenylalanine (for example 3,4-dichlorophenylalanine (3,4-di-Cl-Phe)), alkylphenylalanine (for example 4-methylphenylalanine (4-Me-Phe)), nitrophenylalanine (for example 4-nitrophenylalanine (4-$NO_2$-Phe)), 3-pyridylalanine (3-Pya), 2-thienylalanine (Tha), 2-furylalanine (Fua), 1-naphthylalanine (1-Nal), 2-naphthylalanine (2-Nal), phenylglycine (Phg) and 3-nitrotyrosine (3-$NO_2$-Tyr) residues, $X_2$ and $X_9$ represent a natural or non-natural amino acid residue having the D or L configuration and are independently selected from the amino acid residues having a side chain of aliphatic character represented by the following formula:

(b)

wherein:
$R_{1b}$ represents a hydrogen atom and $R_{2b}$ represents a hydrogen atom or an alkyl or cycloalkyl group, among which residues there may be mentioned more specifically the glycine (Gly), alanine (Ala), valine (Val), leucine (Leu), isoleucine (Ile), 2-aminobutyric acid (Abu), 2-aminoisobutyric acid (Aib), β-cyclohexylalanine (Cha), homoleucine (Hol), norleucine (Nle), norvaline (Nva) and tert-leucine (Tle) residues, $X_5$ and $X_6$ represent a natural or non-natural amino acid residue having the D or L configuration and are independently selected from the amino acid residues that have a side chain capable of establishing ionic interactions represented by the following formula:

(d)

wherein:
$R_{1d}$ represents a hydrogen atom and $R_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, $X_4$, $X_7$, $X_{10}$ and $X_{12}$ represent a natural or non-natural amino acid residue having the D or L configuration and are independently selected from the amino acid residues that have a side chain capable of establishing ionic interactions represented by the following formula:

(d)

wherein:
$R_{1d}$ represents a hydrogen atom and $R_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, or are independently selected from the natural or non-natural amino acid residues having a side chain of aliphatic character represented by the following formula:

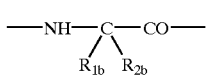
(b)

wherein:

$R_{1b}$ represents a hydrogen atom and $R_{2b}$ represents a hydrogen atom or an alkyl or cycloalkyl group, among which residues there may be mentioned more specifically the glycine (Gly), alanine (Ala), valine (Val), leucine (Leu), isoleucine (Ile), 2-aminobutyric acid (Abu), 2-aminoisobutyric acid (Aib), β-cyclohexylalanine (Cha), homoleucine (Hol), norleucine (Nle), norvaline (Nva) and tert-leucine (Tle) residues, $X_5$ represents a valine residue (Val), $X_8$ and $X_{14}$ independently represent a leucine residue (Leu) having the D or L configuration, $X_{13}$ represents a tryptophan residue (Trp), and $X_{15}$ represents a bond or an arginine residue (Arg), and addition salts thereof with a pharmaceutically acceptable acid or base.

Another advantageous aspect of the invention concerns the compounds of formula (I) wherein:

$Z_1$ represents a hydrogen atom.

$Z_2$ represents a group selected from hydroxy, linear or branched $(C_1-C_6)$-alkoxy, and amino, $X_1$ and $X_{11}$ represent a natural or non-natural amino acid residue having the D or L configuration and are independently selected from the amino acid residues having a side chain of aromatic character represented by the following formula:

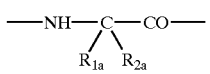
(a)

wherein:

$R_{1a}$ represents a hydrogen atom and $R_{2a}$ represents a cycloalkyl group fused with an unsaturated ring as defined hereinabove, and optionally substituted, or an optionally substituted aryl, optionally substituted arylalkyl, optionally substituted heteroaryl or optionally substituted heteroarylalkyl group, or an imidazolyl or imidazolylalkyl group, among, which residues having a side chain of aromatic character there may be mentioned more specifically the phenylalanine (Phe), histidine (His), tyrosine (Tyr), trptophan (Trp), homophenylalanine (Hof), halophenylalanine (for example 4-chlorophenylalanine (4-Cl-Phe)), dihalophenylalanine (for example 3,4-dichlorophenylalanine (4-di-Cl-Phe)), alkylphenylalanine (for example 4-methylphenylalanine (4-Me-Phe)), nitrophenylalanine (for example 4-nitrophenylalanine (4-NO-Phe)), 3-pyridylalanine (3-Pya), 2-thienylalanine (Tha), 2-furylalanine (Fua), 1-naphthylalanine (1-Nal), 2-naphthylalanine (2-Nal), phenylglycine (Phg) and 3-nitrotyrosine (3-NO$_2$-Tyr) residues, $X_2$ and $X_9$ represent a natural or non-natural amino acid residue having the D or L configuration and are independently selected from the amino acid residues having a side chain of aliphatic character represented by the following formula:

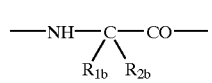
(b)

wherein:

$R_{1b}$ represents a hydrogen atom and $R_{2b}$ represents a hydrogen atom or an alkyl or cycloalkyl group, among which residues there may be mentioned more specifically the glycine (Gly), alanine (Ala), valine (Val), leucine (Leu), isoleucine (Ile), 2-aminobutyric acid (Abu), 2-aminoisobutyric acid (Aib), β-cyclohexylalanine (Cha), homoleucine (Hol), norleucine (Nle), norvaline (Nva) and tert-leucine (Tle) residues, $X_3$ and $X_6$ represent a natural or non-natural amino acid residue having the D or L configuration and are independently selected from the amino acid residues that have a side chain capable of establishing ionic interactions represented by the following formula:

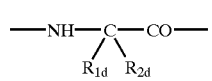
(d)

wherein:

$R_{1d}$ represents a hydrogen atom and $R_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, $X_4$, $X_7$ and $X_{10}$ represent a natural or non-natural amino acid residue having the D or L configuration and are independently selected from the amino acid residues that have a side chain capable of establishing ionic interactions represented by the following formula:

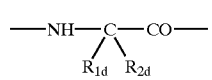
(d)

wherein:

$R_{1d}$ represents a hydrogen atom and $R_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, $X_5$ represents a valine residue (Val), $X_8$ and $X_{14}$ independently represent a leucine residue (Leu) having the D or L configuration, $X_{12}$ represents a natural or non-natural amino acid residue having the D or L configuration, and is selected from the amino acid residues having a side chain of aliphatic character represented by the following formula:

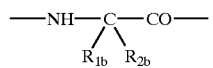
(b)

wherein:

$R_{1b}$ represents a hydrogen atom and $R_{2b}$ represents a hydrogen atom or an alkyl or cycloalkyl group, among which residues there may be mentioned more specifically the glycine (Gly), alanine (Ala), valine (Val), leucine (Leu), isoleucine (Ile), 2-aminobutyric acid (Abu), 2-aminoisobutyric acid (Aib), β-cyclohexylalanine (Cha), homoleucine (Hol), norleucine (Nle), norvaline (Nva) and tert-leucine (Tle) residues, $X_{13}$ represents a tryptophan residue (Trp), $X_{15}$ represents a bond or an arginine residue (Arg), and addition salts thereof with a pharmaceutically acceptable acid or base.

Another advantageous aspect of the invention concerns the compounds of formula (I) wherein:

$Z_1$ represents a hydrogen atom, $Z_2$ represents a group selected from hydroxy, linear or branched ($C_1$–$C_6$)-alkoxy, and amino, $X_1$ and $X_{11}$ represent a natural or non-natural amino acid residue having the D or L configuration and are independently selected from the amino acid residues having a side chain of aromatic character represented by the following formula:

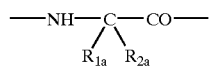
(a)

wherein:

$R_{1a}$ represents a hydrogen atom and $R_2$ represents a cycloalkyl group fused with an unsaturated ring as defined hereinabove, and optionally substituted, or an optionally substituted aryl, optionally substituted arylalkyl, optionally substituted heteroaryl or optionally substituted heteroarylalkyl group, or an imidazolyl or imidazolylalkyl group, among which residues having a side chain of aromatic character there may be mentioned more specifically the phenylalanine (Phe), histidine (His), tyrosine (Tyr), tryptophan (Trp), homophenylalanine (Hof), halophenylalanine (for example 4-chlorophenylalanine (4-Cl-Phe)), dihalophenylalanine (for example 3,4-dichlorophenylalanine (3,4-di-Cl-Phe)), alkylphenylalanine (for example 4-methylphenylalanine (4-Me-Phe)), nitrophenylalanine (for example 4-nitrophenylalanine (4-$NO_2$-Phe)), 3-pyridylalanine (3-Pya), 2-thienylalanine (Tha), 2-furylalanine (Fua), 1-naphthylalanine (1-Nal), 2-naphthylalanine (2-Nal), phenylglycine (Phg) and 3-nitrotyrosine (3-$NO_2$-Tyr) residues, $X_2$ and $X_9$ independently represent an alanine residue (Ala) having the D or L configuration, $X_3$ and $X_6$ represent a natural or non-natural amino acid residue having the D or L configuration and are independently selected from the amino acid residues that have a side chain capable of establishing ionic interactions represented by the following formula:

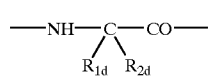
(d)

wherein:

$R_{1d}$ represents a hydrogen atom and $R_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, $X_4$ represents an aspartic acid residue (Asp), $X_5$ represents a valine residue (Val), $X_7$ represents a tyrosine residue (Tyr), $X_8$ and $X_{14}$ independently represent a leucine residue (Leu) having the D or L, configuration, $X_{10}$ represents a glutamine residue (Glu), $X_{12}$ represents an isoleucine residue (Ile), $X_{13}$ represents a tryptophan residue (Trp), $X_{15}$ represents a bond or an arginine residue (Arg), and addition salts thereof with a pharmaceutically acceptable acid or base.

The present invention relates more especially to the peptide compounds of formula (II):

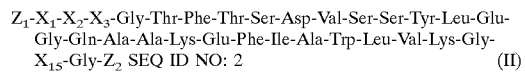
(II)

wherein:

$Z_1$ represents a hydrogen atom, $Z_2$ represents a group selected from hydroxy, linear or branched ($C_1$–$C_6$)-alkoxy, and amino, $X_1$ represents a natural or non-natural amino acid residue having the D or L configuration that has a side chain of aromatic character and is represented by the following formula:

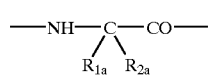
(a)

wherein:

$R_{1a}$ represents a hydrogen atom and $R_{2a}$ represents a cycloalkyl group fused with an unsaturated ring as defined hereinabove, and optionally substituted, or an optionally substituted aryl, optionally substituted arylalkyl, optionally substituted heteroaryl or optionally substituted heteroarylalkyl group, or an imidazolyl or imidazolylalkyl group, among which residues having a side chain of aromatic character there may be mentioned more specifically the phenylalanine (Phe), histidine (His), tyrosine (Tyr), tryptophan (Trp), homophenylalanine (Hof), halophenylalanine (for example 4-chlorophenylalanine (4-Cl-Phe)), dihalophenylalanine (for example 3,4-dichlorophenylalanine (3,4-di-Cl-Phe)), alkylphenylalanine (for example 4-methylphenylalanine (4-Me-Phe)), nitrophenylalanine (for example 4-nitrophenylalanine (4-NO$_2$-Phe)), 3-pyridylalanine (3-Pya), 2-thienylalanine (Tha), 2-furylalanine (Fua), 1-naphthylalanine (1-Nal), 2-naphthylalanine (2-Nal), phenylglycine (Phg) and 3-nitrotyrosine (3-NO$_2$-Tyr) residues, $X_2$ represents a natural or non-natural amino acid residue having the D or L configuration that has a side chain of aliphatic character and is represented by the following formula:

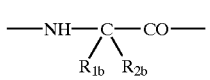

(b)

wherein:
$R_{1b}$ represents a hydrogen atom and $R_{2b}$ represents a hydrogen atom or an alkyl or cycloalkyl group, among which residues there may be mentioned more specifically the glycine (Gly), alanine (Ala), valine (Val), leucine (Leu), isoleucine (Ile), 2-aminobutyric acid (Abu), 2-aminoisobutyric acid (Aib), β-cyclohexylalanine (Cha), homoleucine (Hol), norleucine (Nle), norvaline (Nva) and tert-leucine (Tle) residues, $X_3$ represents a natural or non-natural amino acid residue having the D or L configuration that has a side chain capable of establishing ionic interactions and is represented by the following formula:

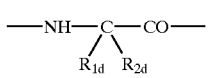

(d)

wherein:
$R_{1d}$ represents a hydrogen atom and $R_{2d}$ represents an aminoalkyl, thioalkyl, hydroxyalkyl, carboxyalkyl, guanidinoalkyl, imidazolyl or imidazolylalkyl group, among which residues there may be mentioned more specifically the aspartic acid (Asp), glutamic acid (Glu), lysine (Lys), arginine (Arg), histidine (His), serine (Ser), threonine (Thr), cysteine (Cys), tyrosine (Tyr), diaminoacetic acid (NH-Gly), diaminobutyric acid (Dab), diaminopropionic acid (Dapa), ornithine (Orn) and methionine (Met) residues, $X_{15}$ represents a bond or an arginine residue, it being understood that the restrictions relating to the compounds defined in formula (I) apply to the compounds of formula (II).

More specifically, in the compounds of formula (II) $X_{15}$ represents a bond.

Amongst the compounds of formula (II), the compounds wherein $X_2$ represents an alanine residue (Ala) having the D or L configuration and $X_{15}$ represents a bond are preferred.

Amongst the preferred compounds of the invention there may be mentioned more especially the following peptides:

His-Ala-Glu-Gly-Thr-Phe-Thr-Ser-Asp-Val-Ser-Ser-Tyr-(D)-Leu-Glu-Gly-Gln-Ala-Ala-Lys-Glu-Phe-Ile-Ala-Trp-Leu-Val-Lys-Gly-Arg-Gly-NH$_2$ SEQ ID NO: 3

Trp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-(D)-Leu-Val-Lys-Gly-Arg-Gly-NH$_2$ SEQ ID NO: 4

Trp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 5

His-Ala-Gln-Gly-Thr-Phe-Thr-Ser-Asp-Val-Ser-Ser-Val-Leu-Glu-Gly-Gln-Ala-Ala-Lys-Glu-Phe-Ile-Ala-Trp-Leu-Val-Lys-Gly-Arg-Gly-NH$_2$ SEQ ID NO: 6

His-Ala-His-Gly-Thr-Phe-Thr-Ser-Asp-Val-Ser-Ser-Val-Leu-Glu-Gly-Gln-Ala-Ala-Lys-Glu-Phe-Ile-Ala-Trp-Leu-Val-Lys-Gly-Arg-Gly-NH$_2$ SEQ ID NO: 7

His-Ala-(D)-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 8

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 9

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 10

His-Leu-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 11

His-Val-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 12

Afp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 13

His-Ala-Asp-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 14

His-Ala-Ser-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 15

His-Ala-Lys-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 16

Phe-(D)-Ala-Glu-Gly-Thr-Phe-Thr-Ser-Asp-Val-Ser-Lys-Tyr-Leu-Glu-Gly-Gln-Ala-Val-Lys-Glu-Phe-Ile-Ala-Trp-Leu-Val-Lys-Gly-Gly-NH$_2$ SEQ ID NO: 17

Phe-(D)-Ala-Gln-Gly-Thr-Phe-Thr-Ser-Asp-Val-Ser-Ser-Val-(D)-Leu-Glu-Gly-Gln-Ala-Ala-Lys-Glu-Phe-Ile-Ala-Trp-Leu-Val-Lys-Gly-Gly-NH$_2$ SEQ ID NO: 18

His-Ala-Leu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 19

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 20

His-Ala-Glu-Gly-Thr-Phe-Thr-Ser-Asp-Val-Ser-Ser-Tyr-Leu-Glu-Gly-Gln-Ala-Ala-Lys-Glu-Trp-Ile-Ala-Trp-Leu-Val-Lys-Gly-Gly-NH$_2$ SEQ ID NO: 21

His-Ala-Glu-Gly-Thr-Phe-Thr-Ser-Asp-Val-Ser-Ser-Tyr-Leu-Glu-Gly-Gln-Ala-Ala-Lys-Glu-Ile-Ile-Ala-Trp-Leu-Val-Lys-Gly-Gly-NH$_2$ SEQ ID NO: 22

His-Ala-Glu-Gly-Thr-Phe-Thr-Ser-Asp-Val-Ser-Ser-Tyr-Leu-Glu-Gly-Gln-Ala-Ala-Lys-Glu-Val-Ile-Ala-Trp-Leu-Val-Lys-Gly-Gly-NH$_2$ SEQ ID NO: 23

His-Ala-Glu-Gly-Thr-Phe-Thr-Ser-Asp-Val-Ser-Ser-Tyr-Leu-Glu-Gly-Gln-Ala-Ala-Lys-Glu-His-Ile-Ala-Trp-Leu-Val-Lys-Gly-Gly-NH$_2$ SEQ ID NO: 24

His-Ala-Glu-Gly-Thr-Phe-Thr-Ser-Asp-Val-Ser-Ser-Tyr-Leu-Glu-Gly-Gln-Ala-Ala-Lys-Glu-Asp-Ile-Ala-Trp-Leu-Val-Lys-Gly-Gly-NH$_2$ SEQ ID NO: 25

His-Ala-Glu-Gly-Thr-Phe-Thr-Ser-Asp-Val-Ser-Ser-Tyr-Leu-Glu-Gly-Gln-Ala-Ala-Lys-Glu-Phe-Leu-Ala-Trp-Leu-Val-Lys-Gly-Gly-NH$_2$ SEQ ID NO: 26

His-Ala-Glu-Gly-Thr-Phe-Thr-Ser-Asp-Val-Ser-Ser-Tyr-Leu-Glu-Gly-Gln-Ala-Ala-Lys-Glu-Phe-Val-Ala-Trp-Leu-Val-Lys-Gly-Gly-NH$_2$ SEQ ID NO: 27

His-Ala-Glu-Gly-Thr-Phe-Thr-Ser-Asp-Val-Ser-Ser-Tyr-Leu-Glu-Gly-Gln-Ala-Ala-Lys-Glu-Phe-Tyr-Ala-Trp-Leu-Val-Lys-Gly-Gly-NH$_2$ SEQ ID NO: 28

His-Ala-Glu-Gly-Thr-Phe-Thr-Ser-Asp-Val-Ser-Ser-Tyr-Leu-Glu-Gly-Gln-Ala-Ala-Lys-Glu-Phe-Arg-Ala-Trp-Leu-Val-Lys-Gly-Gly-NH$_2$ SEQ ID NO: 29

His-Ala-Glu-Gly-Thr-Phe-Thr-Ser-Asp-Val-Ser-Ser-Tyr-Leu-Glu-Gly-Gln-Ala-Ala-Lys-Glu-Phe-Glu-Ala-Trp-Leu-Val-Lys-Gly-Gly-NH$_2$ SEQ ID NO: 30

Phe-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 31

His-Ala-Lys-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 32

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 33

His-Ala-Leu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 34

His-Ala-Ser-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 35

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-(D)-Leu-Val-Lys-Gly-Arg-Gly-NH$_2$ SEQ ID NO: 36.

The invention extends also to a process for the preparation of the compounds of formula (I) which may be obtained by various methods, such as solid phase sequential synthesis, synthesis and coupling of fragments in solution, enzymatic synthesis, or by employing molecular biology techniques.

The general methods of solid phase peptide synthesis have been described by, B. W. Erickson and R. B. Merrifield ("The Proteins", Solid Phase Peptide Synthesis, 3$^{rd}$ edition, 1976, 257).

Solid phase synthesis is carried out using an automatic device which executes in a repetitive and programmable manner the cycles of deprotection, coupling and washing necessary for the sequential introduction of amino acids into the peptide chain.

The C-terminal amino acid is fixed on a resin conventionally used for the preparation of polypeptides, preferably a polystyrene crosslinked with 0.5 to 3.0% divinylbenzene and provided with activated radicals that enable the first amino acid to be fixed covalently to the resin. Appropriate selection of the resin allows the formation after synthesis of a C-terminal carboxylic acid, amide, alcohol or ester function.

The amino acids are then introduced one by one in the order determined by the operator. Each cycle of synthesis corresponding to the introduction of an amino acid comprises N-terminal deprotection of the peptide chain, successive washings designed to remove the reagents or swell the resin, coupling with activation of the amino acid and further washings. Each of those operations is followed by filtration effected as a result of the presence of a sintered glass filter incorporated in the reactor in which the synthesis is beings carried out.

The couplings reagents used are the conventional reagents for peptide synthesis, such as dicyclohexylcarbodiimide (DCC) and hydroxybenzotriazole (HOBT) or benzotriazol-1-yl-oxytris(dimethylamino)phosphonium hexafluorophosphate (BOP), or also diphenyl-phosphorylazide (DPPA).

Activation by the formation of mixed or symmetrical anhydrides is also possible.

Each amino acid is introduced into the reactor in an approximately 6-fold excess in relation to the degree of substitution of the resin and in an approximately equivalent amount in relation to the coupling agents. The coupling reaction may be confirmed at each stage of the synthesis by the ninhydrin reaction test described by E. KAISER et al. (Anal. Biochem., 34, 595, 1970).

After assembling the peptide chain on the resin, an appropriate treatment, for example using a strong acid such as trifluoroacetic acid, or hydrofluoric acid in the presence of anisole, ethanedithiol or 2-methylindole, is used to separate the peptide from the resin and also to free the peptide of its protecting groups. The compound is then purified by conventional purification techniques, especially chromatography techniques.

The peptides of the present invention may also be obtained by coupling in solution selectively protected peptide fragments which may themselves be prepared either in the solid phase or in solution. The use of protecting groups and the exploitation of their differences in stability is analogous to solid phase methods with the exception of the attachment of the peptide chain to the resin. The C-terminal carboxy group is protected, for example, by a methyl ester or an amide function. The methods of activation during coupling are likewise analogous to those employed in solid phase synthesis.

The peptides of the present invention may also be obtained using molecular biology techniques, employing nucleic acid sequences that encode those peptides. Those sequences may be RNA or DNA and may be associated with control sequences and/or inserted into vectors. The latter are then transfected into host cells, for example bacteria. The preparation of the vectors and their production or expression in a host are carried out by conventional molecular biology and genetic engineering techniques.

The synthesis of peptides containing pseudopeptide bonds is carried out either by methods in solution or in combination with solid phase synthesis using conventional methods of organic chemistry. Thus, for example, the introduction of the —$CH_2$—NH bond is effected by preparing Fmoc-NH—CHR—CHO aldehyde in solution according to the technique described by FEHRENTZ and CASTRO (Synthesis, 676–678, 1983) and condensing it with the growing peptide chain either in solid phase according to the technique described by SASAKl and COY (Peptides, 8, 119–121, 1988) or in solution.

The present invention relates also to pharmaceutical compositions comprising as active ingredient at least one compound of the general formula (I) or an addition salt thereof with a pharmaceutically acceptable acid or base, on its own or in combination with one or more inert, non-toxic excipients or carriers.

Amongst the pharmaceutical compositions according to the invention there may be mentioned more especially those which are suitable for oral, parenteral or nasal administration, tablets or dragees, sublingual tablets, sachets, paquets, soft gelatin capsules, suppositories, creams, ointments, dermal gels, transdermal devices, aerosols, drinkable and injectable ampoules.

The dosage varies according to the age and weight of the patient, the nature and severity of the disorder and the route of administration.

The latter may be oral (including the inhalation, gingival and sublingual routes), nasal, rectal, parenteral or transdermal. Generally, the dosage ranges from 10 µg to 500 mg for a treatment of one or more administrations per 24 hours, depending on the administration route and the galenic form used.

The following Examples illustrate the invention without implying any limitation.

By convention, in the Examples below the amino acids in which the abbreviations begin with a capital letter without any other indication, have the L configuration. The amino acids having the D configuration are preceded by the symbol: (D).

EXAMPLE 1

His-Ala-Glu-Gly-Thr-Phe-Thr-Ser-Asp-Val-Ser-Ser-Tyr-(D)-Leu-Glu-Gly-Gln-Ala-Ala-Lys-Glu-Phe-Ile-Ala-Trp-Leu-Val-Lys-Gly-Arg-Gly-NH$_2$ SEQ ID NO: 3

The compound of Example 1 is synthesised on a scale of 0.1 mmole starting from a Fmoc-PAL-PEG-PS resin, using a continuous flow apparatus, in accordance with the following repetitive protocol:

| Operation No. | Operation | Solvent/Reagent | Time |
|---|---|---|---|
| 1 | washing | DMF | 5 min |
| 2 | deprotection | 20% piperidine/DMF | 15 min |
| 3 | washing | DMF | 15 min |
| 4 | coupling | amino acid/DIPCDI/HOBt | 60 min |
| 5 | washing | 20% piperidine/DMF | 5 min |
| 6 | washing | DMF | 5 min |
| 7 | washing | dichloromethane | 5 minz |

Each operation, carried out at ambient temperature, is followed by filtration through a sintered glass filter incorporated in the glass cell (reactor) in which the synthesis is being carried out. The filter retains the resin on which the growing peptide chain is fixed.

Each amino acid (6 equivalents) is assembled using diisopropylcarbodiimide (DIPCDI) in the presence of 1-hydroxybenzotriazole (HOBt) as coupling agent.

After incorporation of the last amino acid, a peptide is obtained which has protected side chains and is fixed on the resin. The support is then dried under a high vacuum for 3 hours. It is subsequently treated with 50 ml of reagent K (trifluoroacetic acid 82.5%, phenol 5%, water 5%, thioanisole 5%, ethanedithiol 2.5%). The mixture is then left at ambient temperature for 12 hours, with occasional stirring and subsequently filtered into an Erlenmeyer flask containing approximately 200 ml of ethyl ether. The peptide precipitates and is isolated by filtration or centrifugation. It is then dried under a high vacuum in the presence of potassium hydroxide pellets for 12 hours, and subsequently purified by preparative HPLC on an reverse phase column (C$_{18}$) using a water/acetonitrile gradient. The fractions containing the peptide are collected and then lyophilised.

Mass spectrum: ESI-MS: m/z=3356.

The following Examples were prepared using the procedure described in Example 1 employing the required amino acids.

EXAMPLE 2

Trp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-(D)-Leu-Val-Lys-Gly-Arg-Gly-NH$_2$ $_2$ SEQ ID NO: 4
Mass spectrum: ESI-MS: m/z=3404.

EXAMPLE 3

Trp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 5
Mass spectrum: ESI-MS: m/z=3404.

EXAMPLE 4

His-Ala-Gln-Gly-Thr-Phe-Thr-Ser-Asp-Val-Ser-Ser-Val-Leu-Glu-Gly-Gln-Ala-Ala-Lys-Glu-Phe-Ile-Ala-Trp-Leu-Val-Lys-Gly-Arg-Gly-NH$_2$ SEQ ID NO: 6
Mass spectrum: ESI-MS: m/z=3290.

EXAMPLE 5

His-Ala-His-Gly-Thr-Phe-Thr-Ser-Asp-Val-Ser-Ser-Val-Leu-Glu-Gly-Gln-Ala-Ala-Lys-Glu-Phe-Ile-Ala-Trp-Leu-Val-Lys-Gly-Arg-Gly-NH$_2$ SEQ ID NO: 7
Mass spectrum: ESI-MS: m/z=3299.

EXAMPLE 6

His-Ala-(D)-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 8
Mass spectrum: ESI-MS: m/z=3184.

EXAMPLE 7

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 9
Mass spectrum: ESI-MS: m/z=3188.

EXAMPLE 8

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 10
Mass spectrum: ESI-MS: m/z=3186.

EXAMPLE 9

His-Leu-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 11
Mass spectrum: ESI-MS: m/z=3241.

EXAMPLE 10

His-Val-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 12
Mass spectrum: ESI-MS: m/z=3227.

EXAMPLE 11

Afp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 13 with Afp representing

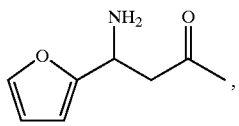

residue corresponding to 3-amino-3-(2-furyl)propanoic acid
Mass spectrum: ESI-MS: m/z=3196.

EXAMPLE 12

His-Ala-Asp-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 14
Mass spectrum: ESI-MS: m/z=3180.

EXAMPLE 13

His-Ala-Ser-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 15
Mass spectrum: ESI-MS: m/z=3152.

EXAMPLE 14

His-Ala-Lys-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 16
Mass spectrum: ESI-MS: m/z=3194.

EXAMPLE 15

Phe-(D)-Ala-Glu-Gly-Thr-Phe-Thr-Ser-Asp-Val-Ser-Lys-Tyr-Leu-Glu-Gly-Gln-Ala-Val-Lys-Glu-Phe-Ile-Ala-Trp-Leu-Val-Lys-Gly-Gly-NH$_2$ SEQ ID NO: 17
Mass spectrum: ESI-MS: m/z=3274.

EXAMPLE 16

Phe-(D)-Ala-Gln-Gly-Thr-Phe-Thr-Ser-Asp-Val-Ser-Ser-Val-(D)-Leu-Glu-Gly-Gln-Ala-Ala-Lys-Glu-Phe-Ile-Ala-Trp-Leu-Val-Lys-Gly-Gly-NH$_2$ SEQ ID NO: 18
Mass spectrum: ESI-MS: m/z=3138.

EXAMPLE 17

His-Ala-Leu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 19
Mass spectrum: ESI-MS: m/z=3178.

EXAMPLE 18

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 20
Mass spectrum: ESI-MS: m/z=3201.

EXAMPLE 19

His-Ala-Glu-Gly-Thr-Phe-Thr-Ser-Asp-Val-Ser-Ser-Tyr-Leu-Glu-Gly-Gln-Ala-Ala-Lys-Glu-Trp-Ile-Ala-Trp-Leu-Val-Lys-Gly-Gly-NH$_2$ SEQ ID NO: 21
Mass spectrum: ESI-MS: m/z=3234.

EXAMPLE 20

His-Ala-Glu-Gly-Thr-Phe-Thr-Ser-Asp-Val-Ser-Ser-Tyr-Leu-Glu-Gly-Gln-Ala-Ala-Lys-Glu-Ile-Ile-Ala-Trp-Leu-Val-Lys-Gly-Gly-NH$_2$ SEQ ID NO: 22
Mass spectrum: ESI-MS: m/z=3162.

EXAMPLE 21

His-Ala-Glu-Gly-Thr-Phe-Thr-Ser-Asp-Val-Ser-Ser-Tyr-Leu-Glu-Gly-Gln-Ala-Ala-Lys-Glu-Val-Ile-Ala-Trp-Leu-Val-Lys-Gly-Gly-NH$_2$ SEQ ID NO: 23
Mass spectrum: ESI-MS: m/z=3146.

EXAMPLE 22

His-Ala-Glu-Gly-Thr-Phe-Thr-Ser-Asp-Val-Ser-Ser-Tyr-Leu-Glu-Gly-Gln-Ala-Ala-Lys-Glu-His-Ile-Ala-Trp-Leu-Val-Lys-Gly-Gly-NH$_2$ SEQ ID NO: 24
Mass spectrum: ESI-MS: m/z=3184.

EXAMPLE 23

His-Ala-Glu-Gly-Thr-Phe-Thr-Ser-Asp-Val-Ser-Ser-Tyr-Leu-Glu-Gly-Gln-Ala-Ala-Lys-Glu-Asp-Ile-Ala-Trp-Leu-Val-Lys-Gly-Gly-NH$_2$ SEQ ID NO: 25
Mass spectrum: ESI-MS: m/z=3162.

EXAMPLE 24

His-Ala-Glu-Gly-Thr-Phe-Thr-Ser-Asp-Val-Ser-Ser-Tyr-Leu-Glu-Gly-Gln-Ala-Ala-Lys-Glu-Phe-Leu-Ala-Trp-Leu-Val-Lys-Gly-Gly-NH$_2$ SEQ ID NO: 26
Mass spectrum: ESI-MS: m/z=3194.

EXAMPLE 25

His-Ala-Glu-Gly-Thr-Phe-Thr-Ser-Asp-Val-Ser-Ser-Tyr-Leu-Glu-Gly-Gln-Ala-Ala-Lys-Glu-Phe-Val-Ala-Trp-Leu-Val-Lys-Gly-Gly-NH$_2$ SEQ ID NO: 27
Mass spectrum: ESI-MS: m/z=3180.

EXAMPLE 26

His-Ala-Glu-Gly-Thr-Phe-Thr-Ser-Asp-Val-Ser-Ser-Tyr-Leu-Glu-Gly-Gln-Ala-Ala-Lys-Glu-Phe-Tyr-Ala-Trp-Leu-Val-Lys-Gly-Gly-NH$_2$ SEQ ID NO: 28
Mass spectrum: ESI-MS: m/z=3245.

EXAMPLE 27

His-Ala-Glu-Gly-Thr-Phe-Thr-Ser-Asp-Val-Ser-Ser-Tyr-Leu-Glu-Gly-Gln-Ala-Ala-Lys-Glu-Phe-Arg-Ala-Trp-Leu-Val-Lys-Gly-Gly-NH$_2$ SEQ ID NO: 29
Mass spectrum: ESI-MS: m/z=3238.

EXAMPLE 28

His-Ala-Glu-Gly-Thr-Phe-Thr-Ser-Asp-Val-Ser-Ser-Tyr-Leu-Glu-Gly-Gln-Ala-Ala-Lys-Glu-Phe-Glu-Ala-Trp-Leu-Val-Lys-Gly-Gly-NH$_2$ SEQ ID NO: 30
Mass spectrum: ESI-MS: m/z=3210.

EXAMPLE 29

Phe-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 31
Mass spectrum: ESI-MS: m/z=3206.

EXAMPLE 30

His-Ala-Lys-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 32
Mass spectrum: ESI-MS: m/z=3255.

EXAMPLE 31

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 33
Mass spectrum: ESI-MS: m/z=3354.

EXAMPLE 32

His-Ala-Leu-Gly-Thr-Phe-Thr-Ser-Asp-Val-Ser-Ser-Val-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 34
Mass spectrum: ESI-MS: m/z=3334.

EXAMPLE 33

His-Ala-Ser-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 35
Mass spectrum: ESI-MS: m/z=3212.

EXAMPLE 34

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-(D)-Leu-Val-Lys-Gly-Arg-Gly-NH$_2$ SEQ ID NO: 36
Mass spectrum: ESI-MS: m/z=3351.

EXAMPLE 35

His-(D)-Ala-Glu-Gly-Thr-Phe-Thr-Ser-Aib-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 37
Mass spectrum: ESI-MS: m/z=3316.

EXAMPLE 36

His-(D)-Ala-Glu-Gly-Thr-Phe-Thr-Ser-Asp-Val-Ser-Ser-Tyr-Leu-Glu-Gly-Gln-Ala-Ala-Lys-Nva-Phe-Ile-Ala-Trp-Leu-Val-Lys-Gly-Gly-NH$_2$ SEQ ID NO: 38
Mass spectrum: ESI-MS: m/z=3165.

EXAMPLE 37

His-(D)-Ala-Glu-Gly-Thr-Phe-Thr-Ser-Asp-Val-Ser-Ser-Tyr-Leu-Glu-Gly-Gln-Ala-Ala-Lys-Nle-Phe-Ile-Ala-Trp-Leu-Val-Lys-Gly-Gly-NH$_2$ SEQ ID NO: 39
Mass spectrum: ESI-MS: m/z=3180.

EXAMPLE 38

His-(D)-Ala-Glu-Gly-Thr-Phe-Thr-Ser-Asp-Val-Ser-Ser-Tyr-Leu-Glu-Gly-Gln-Ala-Ala-Lys-Aib-Phe-Ile-Ala-Trp-Leu-Val-Lys-Gly-Gly-NH$_2$ SEQ ID NO: 40
Mass spectrum: ESI-MS: m/z=3152.

EXAMPLE 39

His-(D)-Ala-Glu-Gly-Thr-Phe-Thr-Ser-Asp-Val-Ser-Ser-Tyr-Leu-Glu-Gly-Gln-Ala-Ala-Lys-Glu-(1)-Nal-Ile-Ala-Trp-Leu-Val-Lys-Gly-Gly-NH$_2$ SEQ ID NO: 41
Mass spectrum: ESI-MS: m/z=3230.

EXAMPLE 40

His-(D)-Ala-Glu-Gly-Thr-Phe-Thr-Ser-Asp-Val-Ser-Ser-Tyr-Leu-Glu-Gly-Gln-Ala-Ala-Lys-Glu-(2)-Nal-Ile-Ala-Trp-Leu-Val-Lys-Gly-Gly-NH$_2$ SEQ ID NO: 42
Mass spectrum: ESI-MS: m/z=3231.

EXAMPLE 41

His-(D)-Ala-Glu-Gly-Thr-Phe-Thr-Ser-Asp-Val-Ser-Ser-Tyr-Leu-Glu-Gly-Gln-Ala-Ala-Lys-Glu-Phg-Ile-Ala-Trp-Leu-Val-Lys-Gly-Gly-NH$_2$ SEQ ID NO: 43
Mass spectrum: ESI-MS: m/z=3133.

EXAMPLE 42

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Nva-Ala-Trp-Leu-Val-Lys-Gly-Gly-NH$_2$ SEQ ID NO: 44
Mass spectrum: ESI-MS: m/z=3180.

EXAMPLE 43

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Nle-Ala-Trp-Leu-Val-Lys-Gly-Gly-NH$_2$ SEQ ID NO: 45
Mass spectrum: ESI-MS: m/z=3115.

EXAMPLE 44

His-(D)-Ala-Glu-Gly-Thr-Phe-Thr-Ser-Aib-Val-Ser-Ser-Tyr-Leu-Glu-Gly-Gln-Ala-Ala-Lys-Aib-(1)-Nal-Nle-Ala-Trp-Leu-Val-Lys-Gly-Gly-NH$_2$ SEQ ID NO: 46
Mass spectrum: ESI-MS: m/z=3158.

Using the process described in Example 1 but replacing the Fmoc-PAL-PEG-PS resin with a Moc-Gly-PAL-PEG-PS resin, the compounds of Examples 45 to 49 are obtained.

EXAMPLE 45

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OH SEQ ID NO: 47
Mass spectrum: ESI-MS: m/z=3192.

EXAMPLE 46

His-(Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OH SEQ ID NO: 48
Mass spectrum: ESI-MS: m/z=3194.

EXAMPLE 47

His-Ala-Asp-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OH SEQ ID NO: 49
Mass spectrum: ESI-MS: m/z=3180.

EXAMPLE 48

Phe-(D)-Ala-Glu-Gly-Thr-Phe-Phe-Thr-Ser-Asp-Val-Ser-Lys-Tyr-Leu-Glu-Gly-Gln-Ala-Val-Lys-Glu-Phe-Ile-Ala-Trp-Leu-Val-Lys-Gly-Gly-OH SEQ ID NO: 50
Mass spectrum: ESI-MS: m/z=3206.

EXAMPLE 49

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OH SEQ ID NO: 51
Mass spectrum: ESI-MS: m/z=3198.

Using the process described in Example 1, but replacing the Fmoc-PAL-PEG-PS resin with a Fmoc-Gly-PAL-PEG-PS resin and replacing reagent K with a triethylamine/methanol mixture, the compounds of Examples 50 to 54 are obtained.

EXAMPLE 50

His-Ala-Glu-Gly-Thr-Phe-Thr-Ser-Asp-Val-Ser-Ser-Tyr-Leu-Glu-Gly-Gln-Ala-Ala-Lys-Glu-Trp-Ile-Ala-Trp-Leu-Val-Lys-Gly-Gly-OH SEQ ID NO: 52
Mass spectrum: ESI-MS: m/z=3210.

EXAMPLE 51

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OCH$_3$ SEQ ID NO: 53
Mass spectrum: ESI-MS: m/z=3212.

EXAMPLE 52

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OCH$_3$ SEQ ID NO: 54
Mass spectrum: ESI-MS: m/z=3209.

EXAMPLE 53

His-Ala-Asp-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OCH$_3$ SEQ ID NO: 55
Mass spectrum: ESI-MS: m/z=3197.

EXAMPLE 54

Phe-(D)-Ala-Glu-Gly-Thr-Phe-Thr-Ser-Asp-Val-Ser-Lys-Tyr-Leu-Glu-Gly-Gln-Ala-Val-Lys-Glu-Phe-Ile-Ala-Trp-Leu-Val-Lys-Gly-Gly-OCH$_3$ SEQ ID NO: 56
Mass spectrum: ESI-MS: m/z=3220.

Using the process described in Example 1, but replacing the Fmoc-PAL-PEG-PS resin with a Fmoc-Gly-PAL-PEG-PS resin and replacing, reagent K with a triethylamine/isopropanol mixture, the compounds of Examples 55 to 57 are obtained.

EXAMPLE 55

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OCH(CH$_3$)$_2$ SEQ ID NO: 57
Mass spectrum: ESI-MS: m/z=3240.

EXAMPLE 56

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OCH(CH$_3$)$_2$ SEQ ID NO: 58
Mass spectrum: ESI-MS: m/z=3238.

EXAMPLE 57

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-OCH(CH$_3$)$_2$ SEQ ID NO: 59
Mass spectrum: ESI-MS: m/z=3237.

PHARMACOLOGICAL STUDY

EXAMPLE A

GLP-1 Receptor Binding Study

The GLP-1 receptor binding studies were carried out using RIN T3 membranes in a 60 ml Tris-HCl buffer pH 7.5 containing 4% BSA and 750 pg/ml of bacitracin. The membranes (20 to 30 µg) are incubated in a final volume of 500 µl with approximately 15 fmol of [125I]-GLP-1 (50,000 cpm) and the cold competitor for 45 min. at 37° C. The reaction is stopped by the addition of 750 µl of cold KRP buffer, pH 7.5, containing 3% BSA. The mixture is centrifuged at 12,000×g (4° C., 5 min). The residue is resuspended in 1 ml of cold KRP buffer and sedimented by a further centrifugation, and the radioactivity is measured. The results are expressed as IC$_{50}$.

Results:

The results obtained indicate that the compounds of the invention have a very high affinity for GLP-1 receptors.

This is true especially of the compound of Example 7, which has an affinity of $3.3 \times 10^{-10}$M.

EXAMPLE B

Determination of the Agonist or Antagonist Character

The agonist character of the compounds of the invention was determined by measuring the production of cyclic AMP after activation of the receptor by the different products being tested.

RIN T3 cells are cultured for 6 days and the culture medium is chanced 1 day before the experiment. The cells ($3 \times 10^5$ per well) are washed twice with DMEM before the addition of 0.5 ml of DMEM containing 1% BSA, 0.2 ml of IBMX and the peptide being tested. After incubation for 20 minutes at 25° C., the intracellular cAMP is extracted, succinylated and quantified by radioimmunoassay.

The reference value of 100% corresponds to the production of cAMP induced by a concentration of $10^{-8}$M GLP-1 and the value 0% corresponds to the basal production in the absence of GLP-1.

The results are expressed as EC$_{50}$, which is the concentration that induces 50% of the production of cAMP obtained using a concentration of $10^{-8}$M GLP-1.

Results:

The compounds of the invention present an agonist character. They increase the production of cAMP and have nanomolar or subnanomolar EC$_{50}$ values. By way of example, the compound of Example 7 has an EC$_{50}$ of $1.02 \times 10^{-9}$M.

EXAMPLE C

Study of the Stimulation of Insulin Production in Cells in Culture

Stimulation of the production of insulin induced by the compounds of the invention is studied using Min6 cells ($5 \times 10^5$ cells per well in 0.5 ml of culture medium). 18 hours before the experiment, the culture medium is pipetted and the cells are washed twice with DRB, pH 7.5, containing 0.1% BSA. The cells are then pre-incubated for one hour in DRB-BSA containing 1 mM glucose and subsequently incubated in DRB-BSA containing different concentrations of glucose and of the compound to be tested. After incubation the mixture is collected, centrifuged for 5 minutes and stored at −20° C. The secretion of insulin is determined by radioimmunoassay using porcine insulin labelled with iodine 125 and guinea pig Kervran anti-insulin antibody.

Results:

The compounds of the invention are capable of stimulating insulin secretion more substantially than 'GLP-1.

EXAMPLE D

Metabolic Stability Study

Each compound is dissolved in 50 mg/ml of BSA in an aqueous 1% trifluoroacetic acid solution to obtain a concentration of 1 mg/ml.

An aliqout of 50 µg/ml of a solution containing the peptide to be studied is incubated in human plasma at 37° C. An HPLC linear analysis method allows measurement of the amount of peptide at time T0, then after incubation for 5, 10, 15, 30 and 60 minutes.

50 µl samples of the above-prepared solution containing 1 mg/ml of the peptide are added to 940 µl of 0.1M TRIS, pH 8.0. After analysis of the solution by HPLC to determine the amount of peptide, 10 µl of an aqueous solution containing 48 milli-units of dipeptidyl peptidase IV (DPP IV) are added, and the samples are analysed by HPLC at time T0 and after incubation for 10 minutes at 37° C.

The measurement results enable evaluation of the amount of peptide remaining and are expressed as a percentage in relation to T0.
Results:

The compounds of the invention appear to exhibit a stability superior to that of the natural peptide.

By way of example, the results obtained with 'GLP-1 and with the compound of Example 7 are compiled in the following Table:

| Compound | Incubation time | Human plasma (% peptide remaining) | DDP IV % peptide remaining |
|---|---|---|---|
| Example 7 | 5 | 100 | — |
|  | 10 | 100 | 100 |
|  | 15 | 100 | — |
|  | 30 | 100 | — |
|  | 60 | 100 | — |
| 'GLP1 | 5 | 83 | — |
|  | 10 | 65 | 8 |
|  | 15 | 53 | — |
|  | 30 | 29 | — |
|  | 60 | 10 | — |

EXAMPLE E

Antihyperglycaemic Activity

The antihyperglycaemic activity of the compounds of the invention was investigated in three-month-old normal male Wistar rats weighing approximately 250 g.

The homeostasis was evaluated by a glucose tolerance test.

Intravenous Glucose Tolerance Test (IVGTT)

Glucose is dissolved in an aqueous 0.9% NaCl solution and administered by the saphenous vein route to rats anaesthetised with pentobarbital (60 mg.kg$^{-1}$, i.p.). Blood samples are collected sequentially from vessels in the tail before and 2, 5, 10, 15, 20 and 30 minutes after the injection of glucose. They are then centrifuged and the plasma is removed. The plasma glucose concentration is determined immediately in an aliquot of 10 µl and the remaining plasma is kept at −20° C. until the insulin concentration is determined by radioimmunoassay.

A single i.v. injection of the product to be tested is given to fasting rats anaesthetised with pentobarbital immediately after loading with glucose in accordance with the protocol described by Hendrick et al. (Metabolism, 1993, 42, 1).

Analytical Methods

The plasma glucose concentration is determined using a glucose analyser (Beckmann Inc., Fullerton, Calif.). The glucose tolerance is measured in relation to two parameters: ΔG and K. ΔG represents the increase in glycaemia above the base line, integrated over a period of 30 minutes, after overloading with glucose at a dose of 1 g/kg.

K is the rate of glucose disappearance between 5 and 30 minutes after administration of the glucose.

The compounds of the invention appear to have an insulin-secretory and antihyperglycaemic activity equivalent or superior to that of 'GLP$_1$, and to have a superior duration of action and a greater metabolic stability in vivo.

EXAMPLE F

Pharmaceutical Composition: Injectable Solution

| | |
|---|---|
| Compound of Example 7 | 10 mg |
| Distilled water for injectable preparations | 25 ml |

We claim:

1. A peptide compound selected from those of formula (I):

$Z_1$-$X_1$-$X_2$-$X_3$-Gly-Thr-Phe-Thr-Ser-$X_4$-$X_5$-Ser-$X_6$-$X_7$-$X_8$-Glu-Gly-Gln-Ala-$X_9$-Lys-$X_{10}$-$X_{11}$-$X_{12}$-Ala-$X_{13}$-$X_{14}$-Val-Lys-Gly-$X_{15}$-Gly-$Z_2$ SEQ ID NO: 1  (I)

wherein:

$Z_1$, substituent of the terminal amino group of the peptide of formula (I), represents hydrogen, alkyl, linear or branched ($C_1$–$C_6$)-acyl, or optionally substituted arylcarbonyl, optionally substituted heteroarylcarbonyl, optionally substituted arylalkylcarbonyl, optionally substituted heteroarylalkylcarbonyl, optionally substituted aryloxycarbonyl, optionally substituted arylalkoxycarbonyl or optionally substituted alkoxycarbonyl, $Z_2$, substituent of the terminal carbonyl group of the peptide of formula (I), represents hydroxy, linear or branched ($C_1$–$C_6$)-alkoxy, or amino (optionally substituted by one or two identical or different groups selected from linear or branched ($C_1$–$C_6$)-alkyl, optionally substituted aryl, optionally substituted heteroaryl, optionally substituted arylcarbonyl, optionally substituted heteroarylcarbonyl, optionally substituted arylalkylcarbonyl and optionally substituted heteroarylalkylcarbonyl, or by two groups that together with the nitrogen atom form a saturated ring having from 5 to 7 ring members), $X_1$ to $X_{14}$ each represents, independently of the others: a natural or non-natural amino acid residue, having the D or L configuration, of the formula:

wherein:

R$_1$ represents hydrogen and R$_2$ represents hydrogen or alkyl, aminoalkyl (optionally substituted on the nitrogen atom by one or two groups selected from alkyl, phenyl, benzyl, cycloalkyl, optionally substituted aryloxycarbonyl, optionally substituted arylalkoxycarbonyl and optionally substituted alkoxycarbonyl), thioalkyl (optionally substituted on the sulphur atom by an alkyl, phenyl, benzyl or cycloalkyl), hydroxyalkyl (optionally substituted on the oxygen atom by alkyl, phenyl, benzyl or cycloalkyl), carboxyalkyl, carbamoylalkyl, guanidinoalkyl, cycloalkyl, cycloalkylalkyl, optionally substituted fused cycloalkyl, optionally substituted aryl, optionally substituted arylalkyl, optionally substituted heteroaryl optionally substituted heteroarylalkyl, imidazolyl or imidazolylalkyl, or R$_1$ and R$_2$, together with the carbon atom carrying them, form cycloalkyl or fused cycloalkyl, or a natural or non-natural cyclic amino acid residue, having the D or L configuration, of the formula:

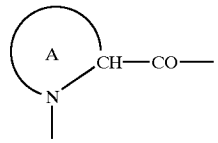

wherein A, together with the nitrogen and carbon atoms to which it is attached, forms a mono- or bi-cyclic group having from 5 to 11 ring members which is saturated, partially unsaturated or unsaturated, and is optionally substituted, or a 3-amino-3-(2-furyl)propanoic acid residue, and $X_{15}$ represents a bond or an arginine residue (Arg), and addition salts thereof with a pharmaceutically acceptable acid or base, with the proviso that:

$X_{15}$ represents a bond when $X_1$ is a residue having the L or D configuration selected from tyrosine (Tyr), arginine (Arg), phenylalanine (Phe), ornithine (Orn), methionine (Met), proline (Pro), leucine (Leu), valine (Val), isoleucine (Ile), alanine (Ala), aspartic acid (Asp), (Gln), histidine (His) and homohistidine, or when $X_2$ represents a residue having the L or D configuration selected from serine (Ser), glycine (Gly), cysteine (Cys), sarcosine (Sar), alanine (Ala), proline (Pro), valine (Val), leucine (Leu), isoleucine (Ile) and threonine (Thr), or when $X_3$ represents an amino acid residue having the L or D configuration selected from glutamine (Gln), aspartic acid (Asp), threonine (Thr), asparagine (Asn) and glutamic acid (Glu), or when $X_5$ represents a tyrosine residue (Tyr), or when $X_6$ represents a lysine residue (Lys), or when $X_{10}$ represents an amino acid residue selected from glutamine (Gln), alanine (Ala), threonine (Thr), serine (Ser) and glycine (Gly), or when $X_{13}$ represents an amino acid residue selected from phenylalanine (Phe), valine (Val), leucine (Leu), isoleucine (Ile), alanine (Ala) and tyrosine (Tyr), wherein:

the residues $X_1$ to $X_{15}$ may not be so selected that the peptide obtained is identical to the natural GLP-1 peptide, the term "alkyl" denotes a linear or branched chain having from 1 to 6 carbon atoms, the term "cycloalkyl" denotes a saturated cyclic hydrocarbon group having from 3 to 8 ring members, the expression "fused cycloalkyl" denotes a bicyclic group having from 8 to 11 ring members composed of a saturated carbon-containing ring fused with a saturated or unsaturated ring optionally comprising one or two hetero atoms selected from nitrogen, oxygen and sulphur, the term "aryl" denotes phenyl, naphthyl or biphenyl, the term "heteroaryl" denotes a mono- or bi-cyclic group having from 5 to 11 ring members and containing from 1 to 4 hetero atoms selected from nitrogen, oxygen and sulphur, for example furyl, pyridyl, thienyl or indolyl, the term "arylcarbonyl" denotes $R_a$—CO—, the term "arylalkylcarbonyl" denotes $R_a$—$R_b$—CO—, the term "heteroarylcarbonyl" denotes $R_c$—CO— and the term "heteroarylalkylcarbonyl" denotes $R_c$—$R_b$—CO—, the term "aryloxycarbonyl" denotes $R_a$—O—CO—, the term "arylalkoxycarbonyl" denotes $R_a$—$R_b$—O—CO— and the term "alkoxycarbonyl" denotes $R_b$—O—CO—, in which groups $R_a$ represents aryl as defined hereinabove, $R_b$ represents alkyl as defined hereinabove and $R_c$ represents heteroaryl as defined hereinabove, the term "substituted" applied to the terms defined above denotes that the groups in question are substituted by one or more halogen or linear or branched ($C_1$-$C_6$)-alkyl, hydroxy, linear or branched ($C_1$-$C_6$)-alkoxy, amino, cyano, nitro or linear or branched ($C_1$-$C_6$)-perhaloalkyl, each peptide bond —CO—NH— may be replaced by a pseudopeptide bond selected from —$CH_2$—NH—, —NH—CO—, —CO—N($CH_3$)—, —$CH_2$—$CH_2$—, —$CH_2$—CO—, —$CH_2$—S—, —$CH_2$—SO—, —$CH_2$—$SO_2$—, —CH═CH— and —CO—$CH_2$—NH—.

2. A compound of claim 1 wherein $Z_1$ represents hydrogen.

3. A compound of claim 1 wherein $Z_2$ represents a group selected from hydroxy, linear or branched ($C_1$-$C_6$)-alkoxy, and amino.

4. A compound of claim 1 wherein $X_{15}$ represents a bond.

5. A compound of claim 1 wherein:

$Z_1$ represents hydrogen, $Z_2$ represents a group selected from hydroxy, linear or branched ($C_1$-$C_6$)-alkoxy, and amino, $X_1$ and $X_{11}$ represent a natural or non-natural amino acid residue having the D or L configuration, and are independently selected from the amino acid residues having a side chain of aromatic character represented by the following formula:

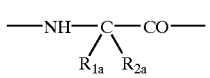

(a)

wherein:

$R_{1a}$ represents hydrogen and $R_{2a}$ represents cycloalkyl fused with an unsaturated ring and optionally substituted, or optionally substituted aryl, optionally substituted arylalkyl, optionally substituted heteroaryl, optionally substituted heteroarylalkyl, imidazolyl or imidazolylalkyl, $X_2$ and $X_9$ represent a natural or non-natural amino acid residue having the D or L configuration and are independently selected from the amino acid residues having a side chain of aliphatic character represented by the following formula:

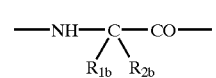

(b)

wherein:

$R_{1b}$ represents hydrogen and $R_{2b}$ represents hydrogen, alkyl or cycloalkyl, $X_3$ and $X_6$ represent a natural or non-natural amino acid residue having the D or L configuration and are independently selected from the amino acid residues represented by the following formula:

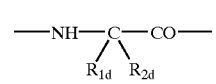

(d)

wherein:

$R_{1d}$ represents hydrogen and $R_{2d}$ represents aminoalkyl, thioalkyl, hydroxyalkyl, carboxyalkyl, guanidinoalkyl, imidazolyl or imidazolylalkyl, $X_4$, $X_7$, $X_{10}$ and $X_{12}$ represent a natural or non-natural amino acid residue having the D or L configuration and are independently selected from the amino acid residues represented by the following formula:

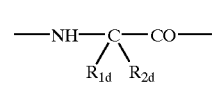

(d)

wherein:

$R_{1d}$ represents hydrogen and $R_{2d}$ represents aminoalkyl, thioalkyl, hydroxyalkyl, carboxyalkyl, guanidinoalkyl, imidazolyl or imidazolylalkyl, or are independently selected from the amino acid residues having a side chain of aliphatic character represented by the following formula:

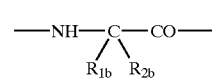

(b)

wherein:

$R_{1b}$ represents hydrogen and $R_{2b}$ represents hydrogen, alkyl or cycloalkyl, $X_5$ represents a valine residue (Val), $X_8$ and $X_{14}$ independently represent a leucine residue (Leu) having the D or L configuration, $X_{13}$ represents a tryptophan residue (Trp), and $X_{15}$ represents a bond or an arginine residue (Arg).

6. A compound of claim 5 wherein $X_{15}$ represents a bond.

7. A compound of claim 1 wherein:

$Z_1$ represents hydrogen, $Z_2$ represents a group selected from hydroxy, linear or branched ($C_1$-$C_6$)-alkoxy, and amino, X₁ and X₁₁ represent a natural or non-natural amino acid residue having the D or L configuration and are independently selected from the amino acid residues having a side chain of aromatic character represented by the following formula:

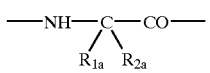
(a)

wherein:

R₁ₐ represents hydrogen and R₂ₐ represents cycloalkyl fused with an unsaturated ring and optionally substituted, or optionally substituted aryl, optionally substituted arylalkyl, optionally substituted heteroaryl, optionally substituted heteroarylalkyl, imidazolyl or imidazolylalkyl, X₂ and X₉ represent a natural or non-natural amino acid residue having the D or L configuration and are independently selected from the amino acid residues having a side chain of aliphatic character represented by the following formula:

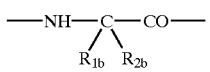
(b)

wherein:

R₁ᵦ represents hydrogen and R₂ᵦ represents hydrogen, alkyl or cycloalkyl,

X₃ and X₆ represent a natural or non-natural amino acid residue having the D or L configuration and are independently selected from the amino acid residues represented by the following formula:

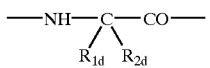
(d)

wherein:

R₁d represents hydrogen and R₂d represents aminoalkyl, thioalkyl, hydroxyalkyl, carboxyalkyl, guanidinoalkyl, imidazolyl or imidazolylalkyl, X₄, X₇ and X₁₀ represent a natural or non-natural amino acid residue having the D or L configuration and are independently selected from the amino acid residues represented by the following formula:

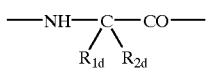
(d)

wherein:

R₁d represents hydrogen and R₂d represents aminoalkyl, thioalkyl, hydroxyalkyl, carboxyalkyl, guanidinoalkyl, imidazolyl or imidazolylalkyl, X₅ represents a valine residue (Val), X₈ and X₁₄ independently represent a leucine residue (Leu) having the D or L configuration, X₁₂ represents a natural or non-natural amino acid residue having the D or L configuration and is selected from the amino acid residues having a side chain of aliphatic character represented by the following formula:

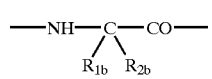
(b)

wherein:

R₁ᵦ represents hydrogen and R₂ᵦ represents hydrogen, alkyl or cycloalkyl,

X₁₃ represents a tryptophan residue (Trp),

X₁₅ represents a bond or an arginine residue (Arg).

8. A compound of claim 7 wherein X₁₅ represents a bond.

9. A compound of claim 1 wherein:

Z₁ represents hydrogen,

Z₂ represents a group selected from hydroxy, linear or branched (C₁–C₆)-alkoxy, and amino, X₁ and X₁₁ represent a natural or non-natural amino acid residue having the D or L configuration and are independently selected from the amino acid residues having a side chain of aromatic character represented by the following formula:

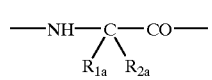
(a)

wherein:

R₁ₐ represents hydrogen and R₂ₐ represents cycloalkyl fused with an unsaturated ring and optionally substituted, an optionally substituted aryl, optionally substituted arylalkyl, optionally substituted heteroaryl, optionally substituted heteroarylalkyl, imidazolyl or imidazolylalkyl, X₂ and X₉ independently represent an alanine residue (Ala) having the D or L configuration, X₃ and X₆ represent a natural or non-natural amino acid residue having the D or L configuration and are independently selected from the amino acid residues represented by the following formula:

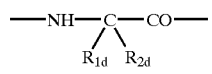
(d)

wherein:

R₁d represents hydrogen and R₂d represents aminoalkyl, thioalkyl, hydroxyalkyl, carboxyalkyl, guanidinoalkyl, imidazolyl or imidazolylalkyl, X₄ represents an aspartic acid residue (Asp), X₅ represents a valine residue (Val), X₇ represents a tyrosine residue (Tyr), X₈ and X₁₄ independently represent a leucine residue (Leu) having the D or L configuration, X₁₀ represents a glutamine residue (Glu), X₁₂ represents an isoleucine residue (Ile), X₁₃ represents a tryptophan residue (Trp), X₁₅ represents a bond or an arginine residue (Arg).

10. A compound of claim 9 wherein X₁₅ represents a bond.

11. A peptide compound of claim 1 selected from those of formula (II):

Z₁-X₁-X₂-X₃-Gly-Thr-Phe-Thr-Ser-Asp-Val-Ser-Ser-Tyr-Leu-Glu-
Gly-Gln-Ala-Ala-Lys-Glu-Phe-Ile-Ala-Trp-Leu-Val-Lys-Gly-
X₁₅-Gly-Z₂ SEQ ID NO: 2                                      (II)

wherein:
$Z_1$, substituent of the terminal amino group of the peptide of formula (II), represents hydrogen,
$Z_2$, substituent of the terminal carbonyl group of the peptide of formula (II), represents hydroxy, linear or branched $(C_1-C_6)$-alkoxy, or amino,
$X_1$ represents a natural or non-natural amino acid residue having the D or L configuration that has a side chain of aromatic character and is represented by the following formula:

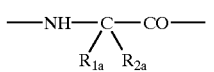
(a)

wherein:
$R_{1a}$ represents hydrogen and $R_{2a}$ represents cycloalkyl fused with an unsaturated ring and optionally substituted, or optionally substituted aryl, optionally substituted arylalkyl, optionally substituted heteroaryl, optionally substituted heteroarylalkyl, imidazolyl or imidazolylalkyl,
$X_2$ represents a natural or non-natural amino acid residue having the D or L configuration that has a side chain of aliphatic character and is represented by the following formula:

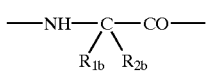
(b)

wherein:
$R_{1b}$ represents hydrogen and $R_{2b}$ represents hydrogen, alkyl or cycloalkyl,
$X_3$ represents a natural or non-natural amino acid residue having the D or L configuration that has a side chain capable of establishing ionic interactions and is represented by the following formula:

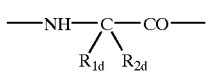
(d)

wherein:
$R_{1d}$ represents hydrogen and $R_{2d}$ represents aminoalkyl, thioalkyl, hydroxyalkyl, carboxyalkyl, guanidinoalkyl, imidazolyl or imidazolylalkyl,
$X_{15}$ represents a bond or an arginine residue.

12. A compound of claim 11 wherein $X_{15}$ represents a bond.

13. A compound of claim 11 wherein $X_2$ represents an alanine residue (Ala) having the D or L configuration and $X_{15}$ represents a bond.

14. A compound of claim 1 selected from:
His-Ala-Glu-Gly-Thr-Phe-Thr-Ser-Asp-Val-Ser-Ser-Tyr-(D)-Leu-Glu-Gly-Gln-Ala-Ala-Lys-Glu-Phe-Ile-Ala-Trp-Leu-Val-Lys-Gly-Arg-Gly-NH₂ SEQ ID NO: 3
Trp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-(D)-Leu-Val-Lys-Gly-Arg-Gly-NH₂ SEQ ID NO: 4
Trp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH₂ SEQ ID NO: 5
His-Ala-Gln-Gly-Thr-Phe-Thr-Ser-Asp-Val-Ser-Ser-Val-Leu-Glu-Gly-Gln-Ala-Ala-Lys-Glu-Phe-Ile-Ala-Trp-Leu-Val-Lys-Gly-Arg-Gly-NH₂ SEQ ID NO: 6
His-Ala-His-Gly-Thr-Phe-Thr-Ser-Asp-Val-Ser-Ser-Val-Leu-Glu-Gly-Gln-Ala-Ala-Lys-Glu-Phe-Ile-Ala-Trp-Leu-Val-Lys-Gly-Arg-Gly-NH₂ SEQ ID NO: 7.

15. A compound of claim 1 selected from:
His-Ala-(D)-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 8
His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 9
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 10
His-Leu-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 11
His-Val-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 12
Afp-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 13
His-Ala-Asp-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 14
His-Ala-Ser-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 15
His-Ala-Lys-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 16
Phe-(D)-Ala-Glu-Gly-Thr-Phe-Thr-Ser-Asp-Val-Ser-Lys-Tyr-Leu-Glu-Gly-Gln-Ala-Val-Lys-Glu-Phe-Ile-Ala-Trp-Leu-Val-Lys-Gly-Gly-NH₂ SEQ ID NO: 17
Phe-(D)-Ala-Gln-Gly-Thr-Phe-Thr-Ser-Asp-Val-Ser-Ser-Val-(D)-Leu-Glu-Gly-Gln-Ala-Ala-Lys-Glu-Phe-Ile-Ala-Trp-Leu-Val-Lys-Gly-Gly-NH₂ SEQ ID NO: 18
His-Ala-Leu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 19
His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH₂ SEQ ID NO: 20
His-Ala-Glu-Gly-Thr-Phe-Thr-Ser-Asp-Val-Ser-Ser-Tyr-Leu-Glu-Gly-Gln-Ala-Ala-Lys-Glu-Trp-Ile-Ala-Trp-Leu-Val-Lys-Gly-Gly-NH₂ SEQ ID NO: 21
His-Ala-Glu-Gly-Thr-Phe-Thr-Ser-Asp-Val-Ser-Ser-Tyr-Leu-Glu-Gly-Gln-Ala-Ala-Lys-Glu-Ile-Ile-Ala-Trp-Leu-Val-Lys-Gly-Gly-NH₂ SEQ ID NO: 22
His-Ala-Glu-Gly-Thr-Phe-Thr-Ser-Asp-Val-Ser-Ser-Tyr-Leu-Glu-Gly-Gln-Ala-Ala-Lys-Glu-Val-Ile-Ala-Trp-Leu-Val-Lys-Gly-Gly-NH₂ SEQ ID NO: 23
His-Ala-Glu-Gly-Thr-Phe-Thr-Ser-Asp-Val-Ser-Ser-Tyr-Leu-Glu-Gly-Gln-Ala-Ala-Lys-Glu-His-Ile-Ala-Trp-Leu-Val-Lys-Gly-Gly-NH₂ SEQ ID NO: 24

His-Ala-Glu-Gly-Thr-Phe-Thr-Ser-Asp-Val-Ser-Ser-Tyr-Leu-Glu-Gly-Gln-Ala-Ala-Lys-Glu-Asp-Ile-Ala-Trp-Leu-Val-Lys-Gly-Gly-NH$_2$ SEQ ID NO: 25

His-Ala-Glu-Gly-Thr-Phe-Thr-Ser-Asp-Val-Ser-Ser-Tyr-Leu-Glu-Gly-Gln-Ala-Ala-Lys-Glu-Phe-Leu-Ala-Trp-Leu-Val-Lys-Gly-Gly-NH$_2$ SEQ ID NO: 26

His-Ala-Glu-Gly-Thr-Phe-Thr-Ser-Asp-Val-Ser-Ser-Tyr-Leu-Glu-Gly-Gln-Ala-Ala-Lys-Glu-Phe-Val-Ala-Trp-Leu-Val-Lys-Gly-Gly-NH$_2$ SEQ ID NO: 27

His-Ala-Glu-Gly-Thr-Phe-Thr-Ser-Asp-Val-Ser-Ser-Tyr-Leu-Glu-Gly-Gln-Ala-Ala-Lys-Glu-Phe-Tyr-Ala-Trp-Leu-Val-Lys-Gly-Gly-NH$_2$ SEQ ID NO: 28

His-Ala-Glu-Gly-Thr-Phe-Thr-Ser-Asp-Val-Ser-Ser-Tyr-Leu-Glu-Gly-Gln-Ala-Ala-Lys-Glu-Phe-Arg-Ala-Trp-Leu-Val-Lys-Gly-Gly-NH$_2$ SEQ ID NO: 29

His-Ala-Glu-Gly-Thr-Phe-Thr-Ser-Asp-Val-Ser-Ser-Tyr-Leu-Glu-Gly-Gln-Ala-Ala-Lys-Glu-Phe-Glu-Ala-Trp-Leu-Val-Lys-Gly-Gly-NH$_2$ SEQ ID NO: 30

Phe-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$ SEQ ID NO: 31

His-Ala-Lys-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 32

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 33

His-Ala-Leu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 34

His-Ala-Ser-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-NH$_2$ SEQ ID NO: 35

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-(D)-Leu-Val-Lys-Gly-Arg-Gly-NH$_2$ SEQ ID NO: 36.

16. A compound of claim 1 which is selected from:

His-Ala-Glu-Gly-Thr-Phe-Thr-Ser-Asp-Val-Ser-Ser-Tyr-(D)-Leu-Glu-Gly-Gln-Ala-Ala-Lys-Glu-Phe-Ile-Ala-Trp-Leu-Val-Lys-Gly-Arg-Gly-NH$_2$, SEQ ID NO: 3 and its addition salts thereof with a pharmaceutically acceptable acid or base.

17. A compound of claim 1 which is selected from:

His-(D)-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$, SEQ ID NO: 9 and its addition salts thereof with a pharmaceutically acceptable acid or base.

18. A compound of claim 1 which is selected from:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$, SEQ ID NO: 10 and its addition salts thereof with a pharmaceutically acceptable acid or base.

19. A compound of claim 1 which is selected from:

His-Ala-Asp-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$, SEQ ID NO: 14 and its addition salts thereof with a pharmaceutically acceptable acid or base.

20. A compound of claim 1 which is selected from:

Phe-(D)-Ala-Glu-Gly-Thr-Phe-Thr-Ser-Asp-Val-Ser-Lys-Tyr-Leu-Glu-Gly-Gln-Ala-Val-Lys-Glu-Phe-Ile-Ala-Trp-Leu-Val-Lys-Gly-Gly-NH$_2$, SEQ ID NO: 17 and its addition salts thereof with a pharmaceutically acceptable acid or base.

21. A compound of claim 1 which is selected from:

His-Ala-Met-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Gly-NH$_2$, SEQ ID NO: 20 and its addition salts thereof with a pharmaceutically acceptable acid or base.

22. A compound of claim 1 which is selected from:

His-Ala-Glu-Gly-Thr-Phe-Thr-Ser-Asp-Val-Ser-Ser-Tyr-Leu-Glu-Gly-Gln-Ala-Ala-Lys-Glu-Phe-Val-Ala-Trp-Leu-Val-Lys-Gly-Gly-NH$_2$, SEQ ID NO: 27 and its addition salts thereof with a pharmaceutically acceptable acid or base.

23. A pharmaceutical composition useful as 'GLP-1 agonist comprising as active principle an amount of a compound as claimed in claim 1, together with one or more pharmaceutically acceptable excipients or vehicles.

24. A method for treating a living body afflicted with a condition selected from non-insulin-dependent type II diabetes, obesity and type I diabetes, comprising the step of administering to the living body an amount of a compound of claim 1 which is effective for alleviation of said condition.

25. A pharmaceutical composition useful in the treatment of non-insulin-dependent type II diabetes, obesity, type I diabetes, comprising as active principle an amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,620,910 B1
DATED : September 16, 2003
INVENTOR(S) : Bernard Calas et al.

It is certified that error appears in the above-identified patent and that said Letters Patent is hereby corrected as shown below:

<u>Title page,</u>
Item [57], ABSTRACT, "$Z_1$- $X_1$- $X_2$- $X_3$- Gly- Thr- Phe- Thr- Ser- $X_4$- $X_5$- Ser- $X_6$- $X_7$- $X_8$ (I)"

should be -- $Z_1$- $X_1$- $X_2$- $X_3$- Gly- Thr- Phe- Thr- Ser- $X_4$- $X_5$- Ser- $X_6$- $X_7$- $X_8$- (I)

Glu- Gly- Gln- Ala- $X_9$- Lys- $X_{10}$- $X_{11}$- $X_{12}$- Ala- $X_{13}$- $X_{14}$- Val- Lys- Gly- $X_{15}$- Gly- $Z_2$ (SEQ ID NO: 1) --; and "$Z_2$ (SEQ ID NO: 1), substituent of the terminal carbonyl" should be -- $Z_2$ substituent of the terminal carbonyl --.

<u>Column 58,</u>
Line 38, insert "glutamic acid (Glu), asparagine (Asn), glutamine" after "(Asp),".

<u>Column 59,</u>
Lines 16 and 17, remove "for example furyl, pyidyl, thienyl or indolyl".

<u>Column</u>

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.      : 6,620,910 B1
DATED           : September 16, 2003
INVENTOR(S)     : Bernard Calas et al.

It is certified that error appears in the above-identified patent and that said Letters Patent is hereby corrected as shown below:

<u>Title page,</u>
Item [57], ABSTRACT, "$Z_1$- $X_1$- $X_2$- $X_3$- Gly- Thr- Phe- Thr- Ser- $X_4$- $X_5$- Ser- $X_6$- $X_7$- $X_8$"

(I)"

should be -- $Z_1$- $X_1$- $X_2$- $X_3$- Gly- Thr- Phe- Thr- Ser- $X_4$- $X_5$- Ser- $X_6$- $X_7$- $X_8$-

(I)

Glu- Gly- Gln- Ala- $X_9$- Lys- $X_{10}$- $X_{11}$- $X_{12}$- Ala- $X_{13}$- $X_{14}$- Val- Lys- Gly- $X_{15}$- Gly- $Z_2$ (SEQ ID NO: 1) --; and "$Z_2$ (SEQ ID NO: 1), substituent of the terminal carbonyl" should be -- $Z_2$ substituent of the terminal carbonyl --.

<u>Column 58,</u>
Line 38, insert "glutamic acid (Glu), asparagine (Asn), glutamine" after "(Asp),".

<u>Column 59,</u>
Lines 16 and 17, remove "for example furyl, pyidyl, thienyl or indolyl".

<u>Column 63,</u>
Lines 64, Claim 14 should read:

14. A compound of claim 1 selected from :

Trp - Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - (D)-Leu - Val - Lys - Gly - Arg - Gly - NH$_2$ SEQ ID NO: 4

Trp - Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Arg - Gly – NH$_2$ SEQ ID NO: 5.

UNITED STATES PATENT AND TRADEMARK OFFICE
CERTIFICATE OF CORRECTION

PATENT NO. : 6,620,910 B1
DATED : September 16, 2003
INVENTOR(S) : Bernard Calas et al.

It is certified that error appears in the above-identified patent and that said Letters Patent is hereby corrected as shown below:

Column 64,
Line 13, Claim 15 should read:

15. A compound of claim 1 selected from :

His - Ala - (D)-Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 8

His - (D)-Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 9

His - Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 10

His - Leu- Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 11

His - Val - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 12

Afp - Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 13

His - Ala - Asp - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 14

His - Ala - Ser - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 15

His - Ala - Lys - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 16

Phe - (D)-Ala - Glu - Gly - Thr - Phe - Thr - Ser - Asp - Val - Ser - Lys - Tyr - Leu - Glu - Gly - Gln - Ala - Val - Lys - Glu - Phe - Ile - Ala - Trp - Leu - Val - Lys - Gly - Gly - NH$_2$ SEQ ID NO: 17

Phe - (D)-Ala - Gln - Gly - Thr - Phe - Thr - Ser - Asp - Val - Ser - Ser - Val - (D)-Leu - Glu - Gly - Gln - Ala - Ala - Lys - Glu - Phe - Ile - Ala - Trp - Leu - Val - Lys - Gly - Gly - NH$_2$ SEQ ID NO: 18

His - Ala - Leu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 19

His - Ala - Met - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 20

His - Ala - Glu - Gly - Thr - Phe - Thr - Ser - Asp - Val - Ser - Ser - Tyr - Leu - Glu - Gly - Gln - Ala - Ala - Lys - Glu - Trp - Ile - Ala - Trp - Leu - Val - Lys - Gly - Gly - NH$_2$ SEQ ID NO: 21

His - Ala - Glu - Gly - Thr - Phe - Thr - Ser - Asp - Val - Ser - Ser - Tyr - Leu - Glu - Gly - Gln - Ala - Ala - Lys - Glu - Ile - Ile - Ala - Trp - Leu - Val - Lys - Gly - Gly - NH$_2$ SEQ ID NO: 22

UNITED STATES PATENT AND TRADEMARK OFFICE
CERTIFICATE OF CORRECTION

PATENT NO.    : 6,620,910 B1
DATED         : September 16, 2003
INVENTOR(S)   : Bernard Calas et al.

It is certified that error appears in the above-identified patent and that said Letters Patent is hereby corrected as shown below:

<u>Column 64 (cont'd),</u>

His - Ala - Glu - Gly - Thr - Phe - Thr - Ser - Asp - Val - Ser - Ser - Tyr - Leu - Glu - Gly - Gln - Ala - Ala - Lys - Glu - Val - Ile - Ala - Trp - Leu - Val - Lys - Gly - Gly - NH$_2$ SEQ ID NO: 23

His - Ala - Glu - Gly - Thr - Phe - Thr - Ser - Asp - Val - Ser - Ser - Tyr - Leu - Glu - Gly - Gln - Ala - Ala - Lys - Glu - His - Ile - Ala - Trp - Leu - Val - Lys - Gly - Gly - NH$_2$ SEQ ID NO: 24

His - Ala - Glu - Gly - Thr - Phe - Thr - Ser - Asp - Val - Ser - Ser - Tyr - Leu - Glu - Gly - Gln - Ala - Ala - Lys - Glu - Asp - Ile - Ala - Trp - Leu - Val - Lys - Gly - Gly - NH$_2$ SEQ ID NO: 25

His - Ala - Glu - Gly - Thr - Phe - Thr - Ser - Asp - Val - Ser - Ser - Tyr - Leu - Glu - Gly - Gln - Ala - Ala - Lys - Glu - Phe - Leu - Ala - Trp - Leu - Val - Lys - Gly - Gly - NH$_2$ SEQ ID NO: 26

His - Ala - Glu - Gly - Thr - Phe - Thr - Ser - Asp - Val - Ser - Ser - Tyr - Leu - Glu - Gly - Gln - Ala - Ala - Lys - Glu - Phe - Val - Ala - Trp - Leu - Val - Lys - Gly - Gly - NH$_2$ SEQ ID NO: 27

His - Ala - Glu - Gly - Thr - Phe - Thr - Ser - Asp - Val - Ser - Ser - Tyr - Leu - Glu - Gly - Gln - Ala - Ala - Lys - Glu - Phe - Tyr - Ala - Trp - Leu - Val - Lys - Gly - Gly - NH$_2$ SEQ ID NO: 28

His - Ala - Glu - Gly - Thr - Phe - Thr - Ser - Asp - Val - Ser - Ser - Tyr - Leu - Glu - Gly - Gln - Ala - Ala - Lys - Glu - Phe - Arg - Ala - Trp - Leu - Val - Lys - Gly - Gly - NH$_2$ SEQ ID NO: 29

His - Ala - Glu - Gly - Thr - Phe - Thr - Ser - Asp - Val - Ser - Ser - Tyr - Leu - Glu - Gly - Gln - Ala - Ala - Lys - Glu - Phe - Glu - Ala - Trp - Leu - Val - Lys - Gly - Gly - NH$_2$ SEQ ID NO: 30

Phe - Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Gly - NH$_2$ SEQ ID NO: 31.

UNITED STATES PATENT AND TRADEMARK OFFICE
CERTIFICATE OF CORRECTION

PATENT NO. : 6,620,910 B1
DATED : September 16, 2003
INVENTOR(S) : Bernard Calas et al.

It is certified that error appears in the above-identified patent and that said Letters Patent is hereby corrected as shown below:

Column 65,
Line 39, Claim 16 should read:
16. A compound which is selected from:

His - Ala - Glu - Gly - Thr - Phe - Thr - Ser - Asp - Val - Ser - Ser - Tyr - (D)-Leu - Glu - Gly - Gln - Ala - Ala - Lys - Glu - Phe - Ile - Ala - Trp - Leu - Val - Lys - Gly - Arg - Gly - NH₂, SEQ ID NO: 3

His - Ala - Gln - Gly - Thr - Phe - Thr - Ser - Asp - Val - Ser - Ser - Val - Leu - Glu - Gly - Gln - Ala - Ala - Lys - Glu - Phe - Ile - Ala - Trp - Leu - Val - Lys - Gly - Arg - Gly - NH₂ SEQ ID NO: 6

His - Ala - His - Gly - Thr - Phe - Thr - Ser - Asp - Val - Ser - Ser - Val - Leu - Glu - Gly - Gln - Ala - Ala - Lys - Glu - Phe - Ile - Ala - Trp - Leu - Val - Lys - Gly - Arg - Gly - NH₂ SEQ ID NO: 7

His - Ala - Lys - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Arg- Gly - NH₂ SEQ ID NO: 32

His - Ala - Met - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Arg - Gly - NH₂ SEQ ID NO: 33

His - Ala - Leu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Arg - Gly - NH₂ SEQ ID NO: 34

His - Ala - Ser - Gly - Thr - Phe - Thr - Ser - Asp - Val - Ser - Ser - Tyr - Leu - Glu - Gly - Gln - Ala - Ala - Lys - Glu - Phe - Ile - Ala - Trp - Leu - Val - Lys - Gly - Arg - Gly - NH₂ SEQ ID NO: 35

His - Ala - Glu - Gly - Thr - Phe - Thr - Ser - Asp - Val - Ser - Ser - Tyr - Leu - Glu - Gly - Gln - Ala - Ala - Lys - Glu - Phe - Ile - Ala - Trp - (D)-Leu - Val - Lys - Gly - Arg - Gly - NH₂ SEQ ID NO: 36 and its addition salts thereof with a pharmaceutically acceptable acid or base.

This certificate supersedes Certificate of Correction issued July 6, 2004.

Signed and Sealed this

Twenty-first Day of September, 2004

JON W. DUDAS
*Director of the United States Patent and Trademark Office*